(12) United States Patent
Joshi et al.

(10) Patent No.: US 8,353,906 B2
(45) Date of Patent: Jan. 15, 2013

(54) ELECTROCHEMICAL PROBE AND METHOD FOR IN SITU TREATMENT OF A TISSUE

(75) Inventors: Ashok V. Joshi, Salt Lake City, UT (US); James Steppan, Park City, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 1314 days.

(21) Appl. No.: 12/052,617

(22) Filed: Mar. 20, 2008

(65) Prior Publication Data
US 2008/0167650 A1 Jul. 10, 2008

Related U.S. Application Data

(63) Continuation-in-part of application No. 11/193,339, filed on Aug. 1, 2005, and a continuation-in-part of application No. 11/616,041, filed on Dec. 26, 2006, now Pat. No. 8,066,659.

(51) Int. Cl.
*A61B 18/04* (2006.01)
(52) U.S. Cl. ........................................................ 606/41
(58) Field of Classification Search ...................... 606/41
See application file for complete search history.

(56) References Cited

U.S. PATENT DOCUMENTS

| | | | |
|---|---|---|---|
| 2,032,723 A | 3/1936 | Schweser | |
| 4,128,173 A | 12/1978 | Lazarus et al. | |
| 4,193,397 A | 3/1980 | Tucker et al. | |
| 4,485,815 A | 12/1984 | Amplatz et al. | |
| 4,632,980 A | 12/1986 | Zee et al. | |
| 4,644,960 A * | 2/1987 | Johans | 607/122 |
| 4,743,199 A | 5/1988 | Weber et al. | |
| 4,938,233 A | 7/1990 | Orrison | |
| 5,052,382 A | 10/1991 | Wainwright | |
| 5,078,714 A * | 1/1992 | Katims | 606/38 |
| 5,106,589 A | 4/1992 | Conrad | |
| 5,163,904 A | 11/1992 | Lampropoulos et al. | |
| 5,439,452 A | 8/1995 | McCarty | |
| 5,536,241 A | 7/1996 | Zapol | |
| 5,540,898 A | 7/1996 | Davidson | |
| 5,674,195 A | 10/1997 | Truthan | |

(Continued)

FOREIGN PATENT DOCUMENTS

DE 447936 7/1927
(Continued)

OTHER PUBLICATIONS

Schell, Laura "Office Action for U.S. Appl. No. 11/193,339 Mailed Jul. 6, 2009", 1-9.

(Continued)

*Primary Examiner* — Roy D Gibson
*Assistant Examiner* — Kaitlyn Smith
(74) *Attorney, Agent, or Firm* — David Fonda

(57) ABSTRACT

A method and apparatus for dehydrating, electro-oxidizing, or electro-reducing a target tissue is described. The apparatus utilizes an electrochemical probe or other device to deliver one or more beneficial agents into the target tissue. Water from the target tissue provides a precursor that may be split by electrolysis to generate the beneficial agent. Alternatively, water is provided from an external source to generate the beneficial agent. The beneficial agent facilitates in situ oxidation and/or reduction of a material within the tissue. One type of beneficial agent is ozone.

25 Claims, 10 Drawing Sheets

U.S. PATENT DOCUMENTS

| | | | |
|---|---|---|---|
| 5,797,872 | A | 8/1998 | Ogata et al. |
| 5,971,722 | A | 10/1999 | Maget et al. |
| 6,071,280 | A * | 6/2000 | Edwards et al. ............ 606/41 |
| 6,073,627 | A | 6/2000 | Sunnen |
| 6,086,552 | A | 7/2000 | Bolton |
| 6,110,431 | A | 8/2000 | Dunder |
| 6,134,806 | A | 10/2000 | Dhaemers |
| 6,136,308 | A | 10/2000 | Tremblay et al. |
| 6,204,058 | B1 | 3/2001 | Bolton |
| 6,251,090 | B1 | 6/2001 | Avery et al. |
| 6,391,183 | B1 | 5/2002 | Tanioka et al. |
| 6,413,228 | B1 | 7/2002 | Hung et al. |
| 6,620,379 | B1 | 9/2003 | Piuk et al. |
| 6,632,222 | B1 * | 10/2003 | Edwards et al. ............ 606/41 |
| 6,800,064 | B2 | 10/2004 | Liang |
| 6,810,288 | B2 | 10/2004 | Joshi |
| 6,875,018 | B2 | 4/2005 | Lynch et al. |
| 6,912,417 | B1 | 6/2005 | Bernard et al. |
| 7,615,030 | B2 | 11/2009 | Murphy et al. |
| 8,066,659 | B2 | 11/2011 | Joshi et al. |
| 8,066,695 | B2 | 11/2011 | Muto et al. |
| 8,162,873 | B2 | 4/2012 | Muto et al. |
| 2002/0037235 | A1 | 3/2002 | Khatchatrian et al. |
| 2002/0133148 | A1 * | 9/2002 | Daniel et al. ............ 606/34 |
| 2002/0188323 | A1 | 12/2002 | Penner et al. |
| 2003/0050674 | A1 | 3/2003 | Joshi |
| 2003/0084907 | A1 * | 5/2003 | Pacek et al. ............ 128/898 |
| 2003/0176834 | A1 | 9/2003 | Horth et al. |
| 2004/0071615 | A1 | 4/2004 | Khatchatrian et al. |
| 2004/0092905 | A1 | 5/2004 | Azzolini |
| 2004/0133188 | A1 | 7/2004 | Vardi et al. |
| 2004/0245087 | A1 | 12/2004 | Lee |
| 2004/0254525 | A1 | 12/2004 | Uber et al. |
| 2005/0010069 | A1 | 1/2005 | Fitchett et al. |
| 2005/0023371 | A1 | 2/2005 | Joshi et al. |
| 2005/0074501 | A1 | 4/2005 | Murphy et al. |
| 2005/0203503 | A1 * | 9/2005 | Edwards et al. ............ 606/33 |
| 2005/0277912 | A1 | 12/2005 | John |
| 2006/0095026 | A1 * | 5/2006 | Ricart et al. ............ 606/32 |
| 2006/0166088 | A1 | 7/2006 | Hokanson et al. |
| 2006/0251551 | A1 | 11/2006 | Johnson |
| 2007/0025890 | A1 | 2/2007 | Joshi et al. |
| 2007/0154363 | A1 * | 7/2007 | Joshi et al. ............ 422/186.04 |
| 2008/0004615 | A1 * | 1/2008 | Woloszko et al. ............ 606/32 |
| 2008/0009847 | A1 * | 1/2008 | Ricart et al. ............ 606/32 |
| 2009/0204062 | A1 | 8/2009 | Muto et al. |
| 2009/0209902 | A1 | 8/2009 | Muto et al. |
| 2010/0307928 | A1 | 12/2010 | Joshi et al. |
| 2010/0312171 | A1 | 12/2010 | Joshi et al. |
| 2012/0022437 | A1 | 1/2012 | Joshi et al. |
| 2012/0022438 | A1 | 1/2012 | Joshi et al. |
| 2012/0150173 | A1 | 6/2012 | Joshi et al. |

FOREIGN PATENT DOCUMENTS

| | | |
|---|---|---|
| DE | 2543284 | 3/1977 |
| WO | WO-96/08280 | 3/1996 |
| WO | WO-98/10774 | 3/1998 |
| WO | WO 01/50983 | 7/2001 |
| WO | WO 02/076533 | 10/2002 |
| WO | WO-2005032387 | 4/2005 |

OTHER PUBLICATIONS

Stigell, Theodore J., "Notice of Allowability for U.S. Appl. No. 10/867,215 Mailed Apr. 7, 2009", 1-4.

Stigell, Theodore J., "Notice of Allowability for U.S. Appl. No. 10/867,215 Mailed on Aug. 6, 2009", 1-4.

Schultz, Ottmar "European Office Action for App. No. EP08/004367 Completed May 7, 2008", 1-6.

Schultz, Ottmar "European Office Action for App. No. EP 08/004372 Completed May 8, 2008", 1-8.

Bumgarner, Melba "Office Action for U.S. Appl. No. 11/616,041 Mailed on Sep. 17, 2009", 1-7.

List of Medizone Patents & Trademarks, http://www.medizoneint.com/patents.html, 1-2.

European Patent Office Automated Translation of DE2543284, (Oct. 5, 2007), 1-4.

Schultz, Abstract and International Search Report for WO2005032387, (Mar. 2, 2005), 1-6.

Andreula, et al., "Interventional Spinal Procedures", *European Journal of Radiology 50*, (2004), 112-119.

Andreula, et al., "Minimally Invasive Oxygen-Ozone Therapy for Lumbar Disk Herniation", *American Journal of Neuroradiology 24*, (2003), 996-1000.

Bocci, "Biological and Clinical Effects of Ozone. Has Ozone Therapy a Future in Medicine?", *British Journal of Biomedical Science 56*, (1999), 270-279.

Bocci, et al., "Ozone in Medicine", *Ozone Science & Engineering 23*, (2001), 207-217.

Bocci, "Oxygen-Ozone Therapy: A Critical Evaluation", *Kluwer Academic Publishers: The Netherlands*, (2002), 43-46.

Bocci, "Ozone:A New Medical Drug", *Springer: The Netherlands*, (2005), 9-11.

McCabe, "Scientific and Medical References Proving Ozone's Validity as a Medical Treatment", http://www.ozonetherapy.co.uk/articles/ed_mccabe_ozone_history_and_references.htm, 1994, Retrieved Oct. 7, 2004, (1994).

Morello, "Ozone Therapy: New Breakthrough for Back Treatment", http://allergytalk.com/6/ca_3.htm, Retrieved Oct. 8, 2007, 1.

Muto, et al., "Percutaneous Treatment of Herniated Lumbar Disc by Intradiscal Oxygen-Ozone Injection", *Interventional Neuroradiology 4* (1998), 279-286.

Sunnen, "Ozone in Medicine Bibliography", http://www.medizoneint.com/biblio.html, (Sep. 1999), 1, 3, 5, 7.

Williams, Office Action for U.S. Appl. No. 10/867,215 sent Jul. 18, 2007, 1-8.

Williams, Office Action for U.S. Appl. No. 10/867,215 sent Aug. 17, 2007, 1-2.

Stigell, Office Action for U.S. Appl. No. 10/867,215 sent Apr. 1, 2008, 1-8.

Stigell, Office Action for U.S. Appl. No. 10/867,215 sent Oct. 16, 2008, 1-6.

Schultz, International Search Report for PCT/IB2004/003706 sent Jun. 3, 2005, 1-16.

Schultz, Written Opinion for PCT/IB2004/003706 sent Jun. 3, 2005, 1-10.

Schell, Office Action for U.S. Appl. No. 11/193,339 sent Dec. 3, 2008, 1-10.

Young, International Search Report for PCT/US06/28425 sent Jul. 31, 2007, 1-2.

Young, Written Opinion for PCT/US06/28525 sent Jul. 31, 2007, 1-4.

Young, International Search Report for PCT/US07/25989 sent Mar. 27, 2008, 1-2.

Young, Written Opinion for PCT/US07/25989 sent Mar. 27, 2008, 1-6.

"Translation of Japanese Office Action", JP App. No. 2008-525006, (Jun. 21, 2011), 1-11.

Jeon, Chang "International Search Report", PCT Application No. 2009/037413, (Nov. 3, 2009), 1-4.

Jeon, Chang "Written Opinion of the International Searching Authority", PCT Application No. 2009/037413, (Nov. 3, 2009), 1-5.

Schell, Laura "Non-Final Office Action", U.S. Appl. No. 11/193,339, (Jan. 19, 2010), 1-9.

Bumgarner, Melba "Non-Final Office Action", U.S. Appl. No. 11/616,041, (Mar. 10, 2010), 1-12.

Stigell, Theodore "Non-Final Office Action", U.S. Appl. No. 12/430,740, (May 26, 2010), 1-8.

Schell, Laura "Final Office Action", U.S. Appl. No. 11/193,339, (Jul. 14, 2010), 1-12.

Osinski, Bradley J., "Notice of Allowance", U.S. Appl. No. 11/616,041, (Aug. 12, 2011), 1-5.

Pfeiffer, Uwe "EP Search Report", App. No. 09722670, (Jun. 17, 2011), 1-6.

Stigell, Theodore "USPTO Office Action", U.S. Appl. No. 12/430,740, (Aug. 12, 2011), 1-9.

Osinski, Bradley "Office Action for U.S. Appl. No. 11/616,041", (May 25, 2011), 1-9.

Osinski, Bradley J., "Office Action for U.S. Appl. No. 11/616,041", (Nov. 5, 2010), 1-11.

Schell, Laura C., "Office Action for U.S. Appl. No. 11/193,339", (Dec. 3, 2008),1-10.

Stigell, Theodore J., "Office Action for U.S. Appl. No. 12/430,740", (Oct. 14, 2010),1-11.

Stigell, Theodore J., "Office Action for U.S. Appl. No. 12/430,740", (Feb. 22, 2011),1-6.

Stigell, Theodore J., "Office Action for U.S. Appl. No. 12/431,089", (Feb. 18, 2011),1-7.

Stigell, Theodore J., "Non-Final Office Action", U.S. Appl. No. 12/431,062, (Jul. 11, 2012),1-8.

Schell, Laura C., "Non-Final Office Action", U.S. Appl. No. 11/193,339,(Jul. 20, 2012),1-9.

Singh, Vijay "Examiner's First Report on Patent Application 2007342491", Australian Patent Application 2007342491, (May 15, 2012),1-3.

McTavish, Megan "Notice of Requisition", CA App. No. 2,612,541 (Corresponding to U.S. Appl. No. 11/193,339, (Jul. 9, 2012),1-2.

Stigell, Theodore J., "Non-Final Office Action", Non-Final Office Action of U.S. Appl. No. 12/429,736, (Nov. 4, 2011),1-7.

Stigell, Theodore J., "Final Office Action", Final Office Action for U.S. Appl. No. 12/429,736, (Feb. 21, 2012),1-8.

Stigell, Theodore J., "Non-Final Office Action", Non-Final Office Action for U.S. Appl. No. 12/431,062, (Jan. 18, 2012),1-10.

Umehara, Makiko "Examiner's First Report (AU)", Examiner's First Report for AU application No. 2010206008 (corresponding to U.S. Appl. No. 12/429,736, (Feb. 24, 2011),1-2.

Umehara, Makiko "Examiners Report No. 2 (AU)", Examiners Report No. 2 (AU) for app. No. 2010204467 (corresponding to U.S. Appl. No. 12/430,740, (Mar. 29, 2012),1-2.

McTavish, Megan "Office Action (CA)", Office Action/Notification of Requisition (CA) for app. No. 2612541 (corresponding to U.S. Appl. No. 11/193,339, (Aug. 25, 2011),1-3.

Tanaka, Reiko "Notice of Reasons for Rejection", Notice of Reasons for Rejection (JP) and Translation for app. No. 2009-544036 (corresponding to U.S. Appl. No. 11/616,041, (Jan. 24, 2012),1-8.

\* cited by examiner

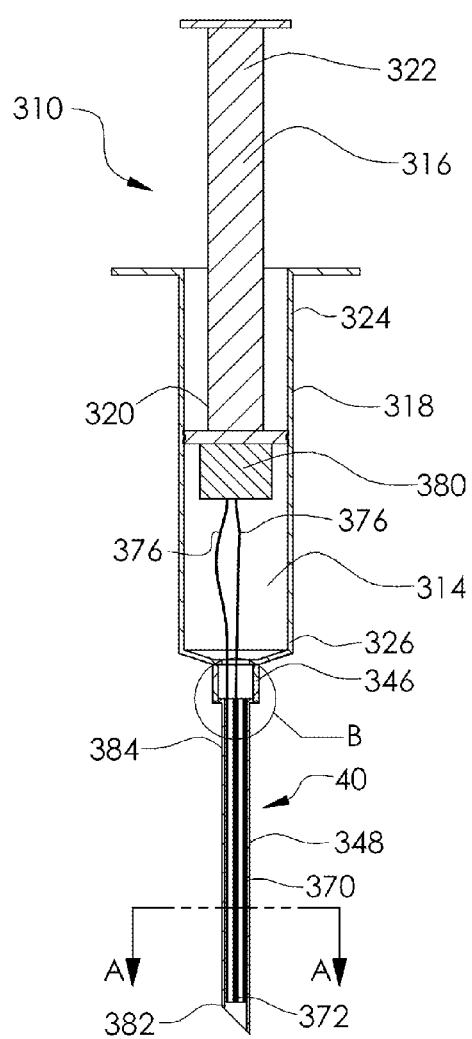
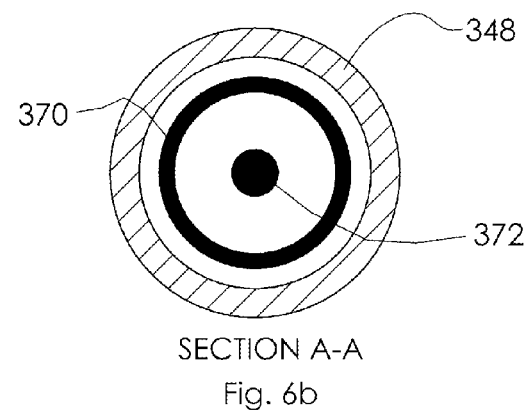
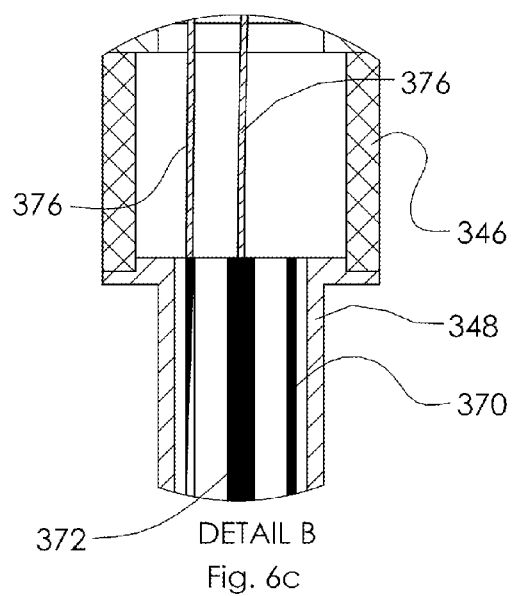
SECTION A-A
Fig. 6b
DETAIL B
Fig. 6c
Fig. 6a

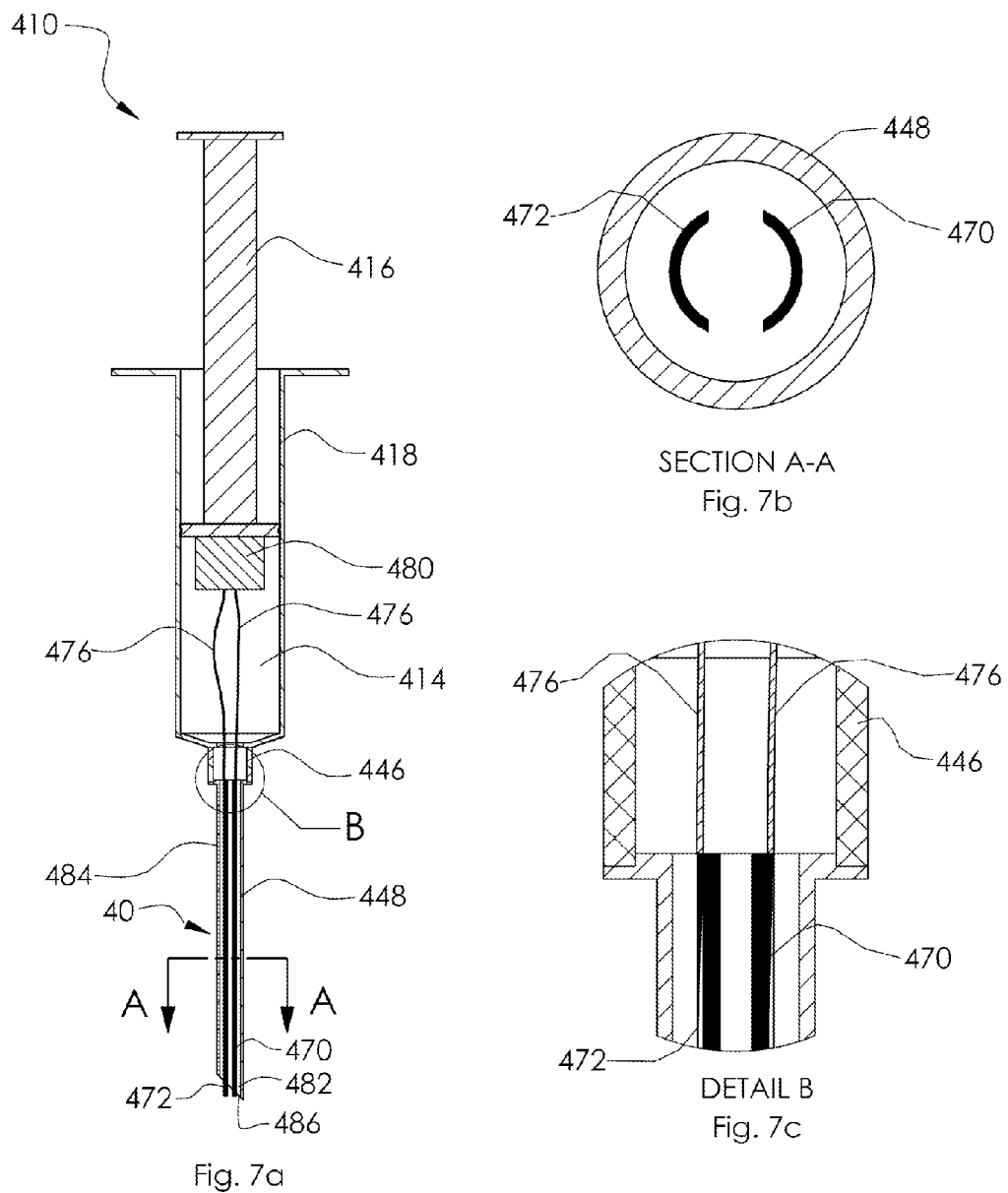

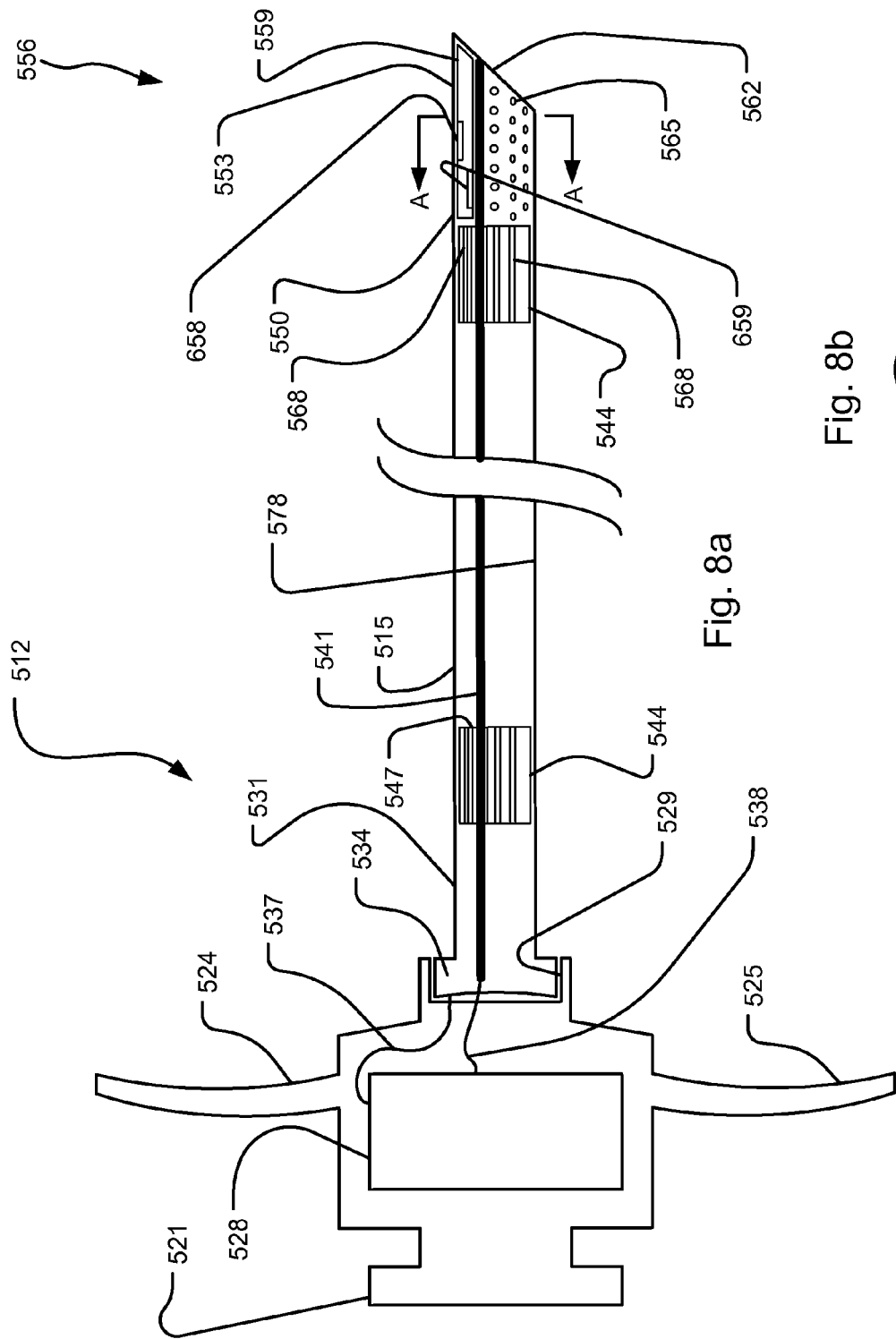
Fig. 8a
Fig. 8b

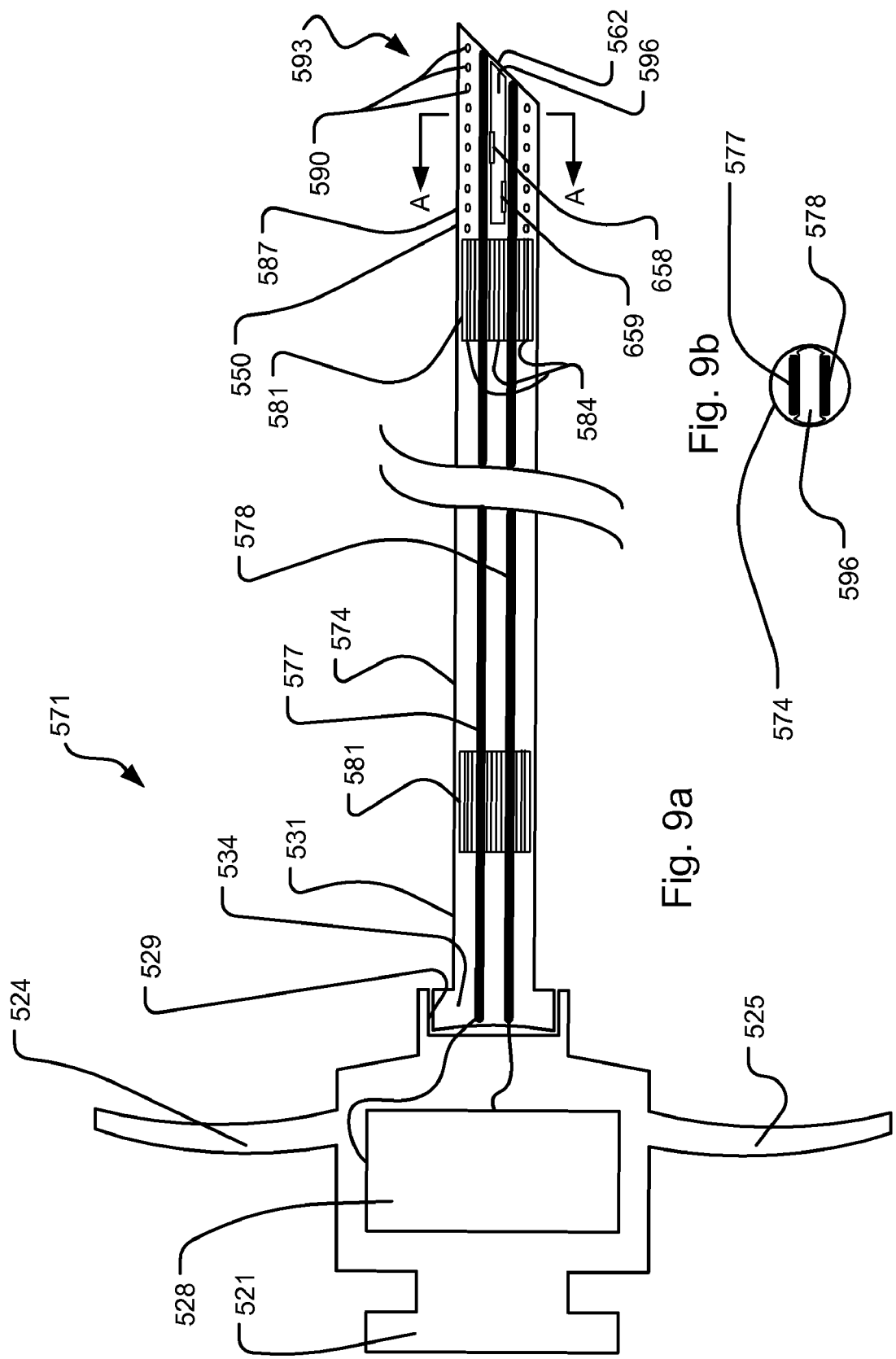

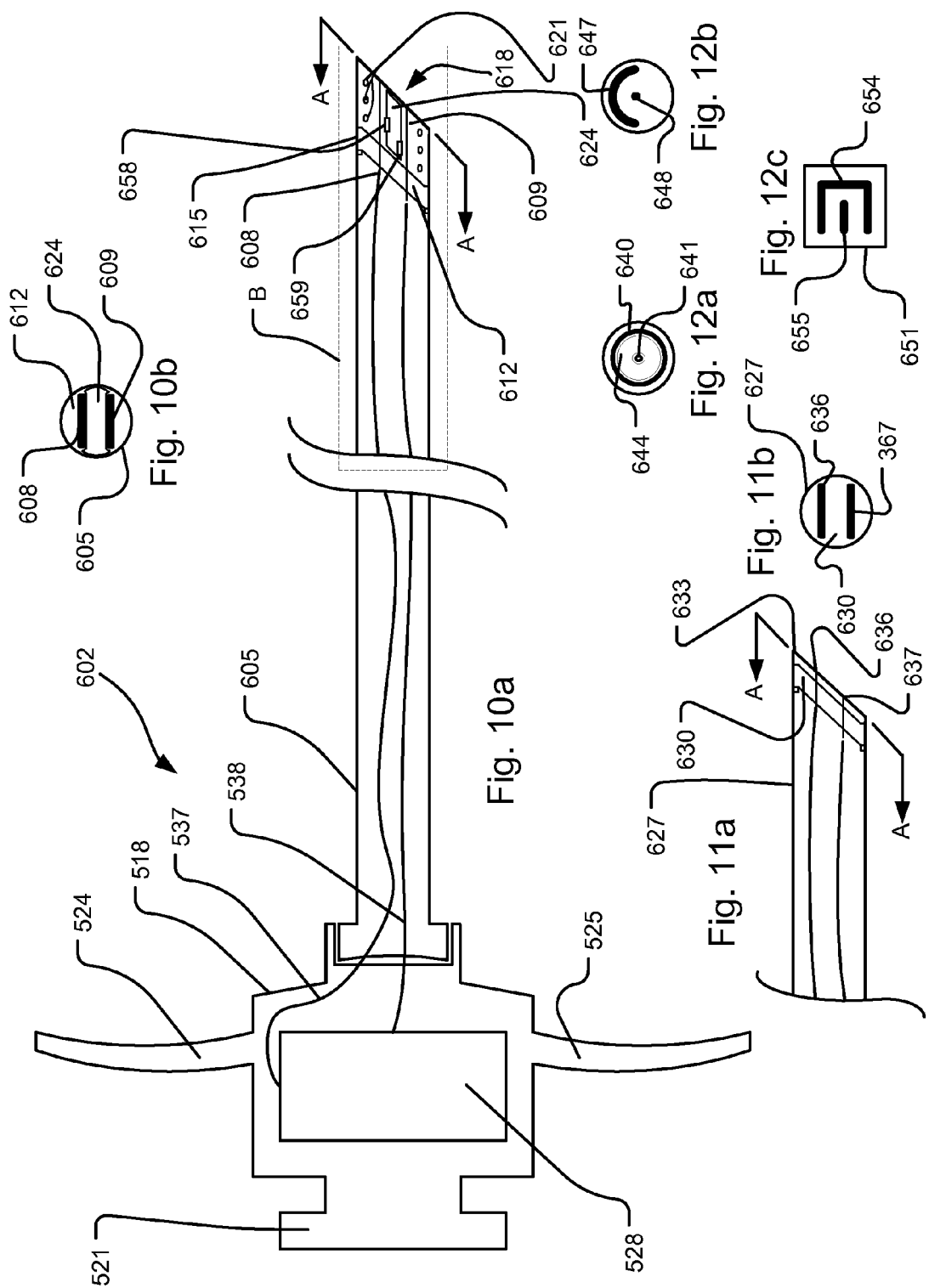

ELECTROCHEMICAL PROBE AND METHOD FOR IN SITU TREATMENT OF A TISSUE

CROSS-REFERENCE TO RELATED APPLICATIONS

This application is a continuation-in-part of U.S. patent application Ser. No. 11/193,339 filed on Aug. 1, 2005, and a continuation-in-part of U.S. patent application Ser. No. 11/616,041 now U.S. Pat. No. 8,066,659 filed Dec. 26, 2006, both of which are incorporated by reference herein in their entirety.

BACKGROUND

The present invention relates generally to an apparatus for treating a tissue and in particular, for dehydrating, electro-oxidizing, or electro-reducing a material of the tissue. The present invention also relates to creation and administration of a fluidic therapeutic agent into the tissue.

Back joint disc or tendon pain is a common and potentially debilitating ailment that affects an estimated 80% of the worldwide population at least once in a lifetime. In many instances, the cause of the pain can be attributed to a degenerated intervertebral disc that has further deteriorated into a condition known as disc herniation. This occurs when the disc nucleus pulposus extrudes through a tear or fissure in the outer lining of the disk, thereby exerting pressure on spinal nerves. The compression caused by the herniated nucleus leads to inflammation and is directly responsible for the pain felt, which in some cases extends down the leg (also referred to as sciatica). Available treatments for this type of back pain vary according to the severity of the hernia. If mild, the patient's condition can be treated with rest and inactivity for an extended period of time. However, for patients suffering from a severe herniation or who do not respond to non-invasive treatment (pharmacological and/or physical therapy), surgical intervention is often recommended. With this invasive treatment come several disadvantages such as: i) irreversibility of the procedure; ii) formation of scar tissue; iii) slower recovery time; iv) longer hospital stays; v) risk of infection.

Since the late 1950s, many attempts have been made to treat sciatica and lower back pain, by reducing the volume of the disc, with minimally invasive percutaneous procedures to avoid surgery. Well known treatments, for example, are percutaneous discetomy, percutaneous plasma disc decompression (nucleoplasty), intradiscal electrothermal therapy (IDET), and percutaneous intradiscal radiofrequency thermocoagulation (PIRT). However, the high costs of these procedures have kept researchers looking for another alternative. Unfortunately, these conventional treatments use procedures that ablate, burn, cut, and that are relatively harsh for the target tissues, and often for surrounding tissues, while attempting to reduce volume of the target tissues.

For other conditions such as rheumatoid arthritis, osteoarthritis or a repetitive injury through sports or occupation, such as tennis elbow, frozen shoulder, or house maids knee, inflammation can develop between the two surfaces that are involved in allowing joint function, such as a tendon and the sheath or lubricated tube in which that tendon moves. Inflammation such as bursitis in the knee shoulder hip, or other anatomic bursa may benefit from the administration of a therapeutic agent such as oxygen-ozone mixtures or excited, energetic, pure oxygen. Such inflammation includes epicondylitis, and other tendonitis and bursitis, including the wrist, hand and the tendon sheaths of the hand and wrist. Inflammation can occur at a site where a tendon or a ligament insert to bone or pass through a sheath from trauma, tension, over use or disease.

Inflammation can develop through pathologies of any joint, and these may include the inflammatory arthropatic conditions of rheumatoid arthritis, psoriatic arthritis and the like, or osteoarthritis. Joints that are subject to these maladies and that are amenable to the administration of a therapeutic agent such as oxygen-ozone mixtures or excited, energetic, pure oxygen include the synovial joints such as the temperomandibular joint, the hip joint, knee joint, ankle joint, elbow joint or sacro-iliac joint. Vertebral facet and sacro-iliac joints may also benefit. Inflammation of joints in the hand, wrist and feet with rheumatoid arthritis, osteoarthritis or a repetitive injury through sports or occupationally caused injuries such as carpal tunnel syndrome, may likewise benefit from treatment.

The inflammatory and arthritic or degenerative conditions discussed and described above are usually treated with a combination of anti-inflammatory agents such as ibuprofen, or more powerful drugs such as steroids or chemotherapy such as methotrexate. It is a common medical practice to inject steroid medications or lidocaine directly into the inflamed tissue or joint. This is often done repeatedly. These drugs can be associated with side effects of infection and even death from gastric ulcer bleeding or immunosurpression and infection. Some skilled in the art believe that ozone therapy whether with oxygen-ozone mixtures or excited, energetic, pure oxygen as a gas or dissolved in a liquid has advantages over the current practices.

Lavage of a surgical space prior to placement of a permanent surgical implant such as a hip or knee prosthesis, or pacemaker or treatment of an infected joint can be facilitated by the use of oxygen-ozone mixtures or excited, energetic, pure oxygen as a sterilizing substance. Similarly, a colostomy stoma can be created such that the adhesive disk is infused with oxygen-ozone mixtures or excited, energetic, pure oxygen as a gas or dissolved in a liquid to aid in healing and inhibit infection. The post surgical recovery from sternotomy after cardiac surgery is often complicated by wound infection. Placement of a resorbable catheter in the wound that could be irrigated with oxygen-ozone mixtures or excited, energetic, pure oxygen as a gas or oxygen dissolved in a liquid would aid healing. Indeed, any wound could have a resorbable multisided hole catheter placed in it to allow oxygen-ozone mixtures or excited, energetic, pure oxygen to be injected through it. This would have anti-infective, analgesic, and wound-healing properties thereby shortening recovery time and decreasing complication rates after surgery.

Endoscopic procedural infusion of ozone and trans catheter infusion of ozone can be used to inhibit the complications from endoscopic medical intervention or image guided or non-image guided catheter based intervention, such as for example, in endoscopic evaluation of the pancreatic duct.

Dental injection of oxygen-ozone mixtures or excited, energetic, pure oxygen as a gas or dissolved in a liquid may augment the preparation and repair of dental cavities, and aid in reduction of root canal inflammation or periodontal disease.

There are veterinary applications of minimally invasive administration of oxygen-ozone mixtures or excited, energetic, pure oxygen as a gas or dissolved in a liquid in animals diseased with disc and degenerative syndromes. Few other options are available in that arena. Some animals are destroyed due to debilitating pain from disc disease, and arthritis.

SUMMARY

Embodiments of equipment specifically designed for the treatment of disc herniation and other medical conditions affecting the body are described. Such equipment uses oxygen-ozone mixtures or excited, energetic, pure oxygen so that treatment can be done in an efficient and sterile manner. In some embodiments, kits that are portable, disposable, or reusable are described to provide sterile, stable, ozone rapidly on demand for intervention in inflammatory and degenerative disease. Embodiments of the equipment facilitates treatments of target tissue that are less harsh than conventional procedures and which have the ability to reduce volume that is due to herniation and/or inflammation of tissues and associated membranes.

Embodiments of a method are described. In one embodiment, the method is a method of treating a tissue. An embodiment of the method includes inserting a pair of electrodes into the tissue in a body. The method also includes applying a low frequency voltage to a pair of electrodes and causing in situ electrolysis within the tissue in the body. This is done by applying the low frequency voltage to the pair of electrodes. In some embodiments, causing the in situ electrolysis includes dehydrating the tissue by forming at least one of hydrogen and hydrogen ions, and forming at least one of oxygen, ozone, and oxygen ions. In some embodiments, causing the in situ electrolysis includes causing electro-oxidation of a material of the tissue. Alternatively, the in situ electrolysis may cause electro-reduction of the material of the tissue. In some embodiments, the method also includes placing an absorbent membrane between the pair of electrodes, at least partially filling the absorbent membrane with a fluid, and electrolyzing the fluid in the absorbent membrane. The fluid may be water from within the tissue or water from a source outside of the tissue. Other embodiments of the method are also described.

Embodiments of an apparatus are also described. In one embodiment, the apparatus is an electrochemical probe for treating a tissue in a body. An embodiment of the electrochemical probe includes a needle, a material treatment module, and a power source. The needle includes a tip to penetrate tissue within the body. The material treatment module is located in the tip of the needle. The material treatment module includes first and second electrodes to electrolyze an electrolyte between the first and second electrodes. The electrolyte may include water from within our outside of the tissues or other fluids such as organic solvents. The power source supplies a low frequency electrical potential to the first and second electrodes. In some embodiments, an absorbent membrane is disposed between the first and second electrodes. The membrane is configured to at least partially contain the electrolyte. Other embodiments of the apparatus are also described.

Other aspects and advantages of embodiments of the present invention will become apparent from the following detailed description, taken in conjunction with the accompanying drawings, which are illustrated by way of example of the various principles and embodiments of the invention.

BRIEF DESCRIPTION OF THE DRAWINGS

The present embodiments will become more fully apparent from the following description and appended claims, taken in conjunction with the accompanying drawings. It is to be understood that the accompanying drawings depict only typical embodiments, and are, therefore, not to be considered to be limiting of the scope of the present disclosure. The embodiments will be described and explained with specificity and detail in reference to the accompanying drawings as set forth below.

FIG. 6a is a cutaway plan view of an alternative embodiment of the invention.

FIG. 6b is cross-sectional plan view of FIG. 6a taken along line A-A.

FIG. 6c is detailed plan view of section B of FIG. 6a.

FIG. 7a is a cutaway plan view of an alternative embodiment of the invention.

FIG. 7b is cross-sectional plan view of FIG. 7a taken along line A-A.

FIG. 7c is detailed plan view of section B of FIG. 7a.

FIG. 8a is a diagrammatic sectional view of an embodiment of an electrochemical probe.

FIG. 8b is a diagrammatic cross sectional view of the electrochemical probe of FIG. 9a taken along section A-A.

FIG. 9a is a diagrammatic sectional view of another embodiment of an electrochemical probe.

FIG. 9b is a diagrammatic cross sectional of the electrochemical probe of FIG. 9a view taken along section A-A.

FIG. 10a is a diagrammatic sectional view of another embodiment of an electrochemical probe.

FIG. 10b is a diagrammatic cross sectional view of the electrochemical probe of FIG. 10a taken along section A-A.

FIG. 11a is a partial diagrammatic sectional view of another embodiment of a portion of the electrochemical probe of FIG. 10a corresponding to region B outlined by a dashed line.

FIG. 11b is a diagrammatic cross sectional view (or end view) of the electrochemical probe of FIG. 11a taken along section A-A.

FIGS. 12a-12c are diagrammatic cross sectional views (or end views) of alternative embodiments that may be substituted for any of the embodiments shown in FIGS. 8a-11b.

Throughout the description, similar reference numbers may be used to identify similar elements.

DETAILED DESCRIPTION

Figure 1:
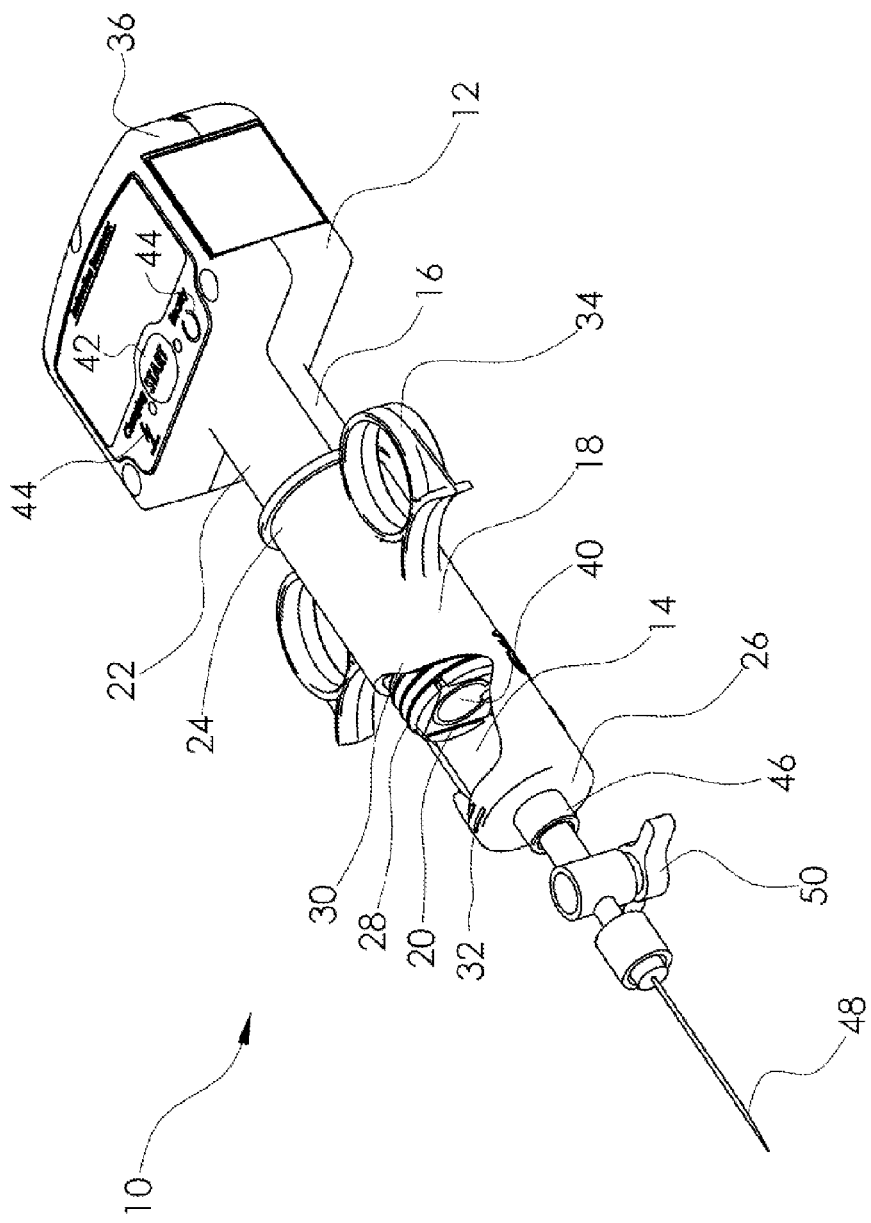
FIG. 1 is a partially cutaway perspective view of an apparatus for administering a therapeutic agent in accordance with an embodiment of the invention.

In the following description, specific details of various embodiments are provided. However, some embodiments may be practiced without at least some of these specific details. In other instances, certain methods, procedures, components, and circuits are not described in detail for the sake of brevity and clarity.

Although certain functionality is described herein with respect to each of the illustrated components of the electrochemical probe or other tissue treatment apparatus or system, other embodiments of the apparatuses and methods may implement similar functionality using fewer or more components. Additionally, some embodiments of the apparatuses and systems described herein may implement more or less functionality than is described herein.

The present invention may be embodied in other specific forms without departing from its spirit or essential characteristics. The described embodiments are to be considered in all respects only as illustrative and not restrictive. While the various aspects of the embodiments are presented in drawings, the drawings are not necessarily drawn to scale unless specifically indicated. The scope of the invention is, therefore, indicated by the appended claims rather than by the foregoing description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

In the following description, numerous specific details are provided, such as examples of housings, barriers, chambers etc., to provide a thorough understanding of embodiments of the invention. One skilled in the relevant art will recognize, however, that the invention can be practiced without one or more of the specific details, or with other methods, components, materials, and so forth. In other instances, well-known structures, materials, or operations such as vacuum sources are not shown or described in detail to avoid obscuring aspects of the invention.

Referring now to the FIG. 1, a handheld dispensing apparatus 10 according to the present invention is shown. The apparatus 10 includes a housing 12 that defines a chamber 14. In one embodiment, the apparatus 10 or housing 12 includes a plunger 16 and a barrel 18 that define the chamber. The plunger has a first end 20 and a second end 22. The barrel 18 has a first end 24 that is open for receiving the first end 20 of the plunger 16 such that the barrel 18 movably engages the plunger 16. The barrel 18 also includes a second end 26. In the illustrated embodiment, the first end 20 of the plunger 16 and the second end 26 of the barrel 18 form the chamber 14. The housing 12 may have a volume of less than about 150 cubic centimeters. In one embodiment, the chamber 14 can hold a volume of material up to about 150 cubic centimeters. In another embodiment, the chamber 14 can hold a volume of no less than about 0.1 cubic centimeters. It will be appreciated that the range of volumes may coincide with the position of the plunger 16 within the barrel 18. For example, the plunger 16 may move within the barrel 18 between a fill position, where the first end 20 of the plunger 16 is within the first end 24 of the barrel 18, but not completely within the barrel 18, and a dispensing position, where the first end 20 of the plunger 16 is substantially within the barrel 18 such that the first end 20 of the plunger 16 is adjacent the second end 26 of the barrel 18.

The chamber 14 is configured to retain a material. "Material," as used throughout this specification, means gas, liquid, gels, solids, or combinations thereof. Material may also be solids suspended or dispersed throughout liquids, gases, or gels. A precursor or starting material may be charged into the device to be treated by operation of the device to create a beneficial or therapeutic agent. Accordingly, the device 10 can be used to create treated material that acts as a beneficial agent. As used throughout this disclosure, "precursor," "precursor material," and "starting material" are used synonymously. Additionally, "treated material," "beneficial agent," and "therapeutic agent" may be used synonymously. The device is used to make a precursor material into a beneficial agent and then deliver the beneficial agent to a desired place, usually within a body.

In one embodiment, the first end 20 of the plunger may be configured with a seal 28 to facilitate retention of the material within the chamber 14. The seal may be a gasket or flexible flange or other mechanical means known in the art. It will be appreciated by those of skill in the art that there are a variety of ways to retain material within the chamber 14, each of which are within the scope of this invention. An outer surface 30 of the barrel 18 may include graduations 32 to measure the amount of material in the chamber 14. The device 10 may be configured in such a way to facilitate moving the plunger 16 between the fill position and the dispensing position. For example, the barrel 18 may include a handle and finger holds 34, and the plunger 16 may be configured with a handle 36.

In one embodiment, the apparatus 10 includes a material treatment module 40. As will be discussed in greater detail in connection with FIGS. 3 and 4 below, the material treatment module 40 can take a variety of configurations. The material treatment module 40 may be positioned within the housing 12 or the barrel 18. In one embodiment, the material treatment module 40 is positioned within the plunger 16. In other embodiments, the material treatment module 40 may be positioned within the barrel 18. In still other embodiments, the material treatment module 40 may be positioned outside the housing 12.

The material treatment module 40 is in operable communication with the chamber 14 such that precursor material in the chamber may come into contact with, and be treated by, the material treatment module 40. As used throughout this specification, the treating or treatment of material means to alter the composition or properties of all or a portion of the material. Similarly, "treated material" means material that has had its chemical composition or other properties altered or modified. For example, in an embodiment where the precursor material is oxygen, the material treatment module 40 may be an ozone generator for creating ozone and the resulting or treated material may be a mixture of oxygen and ozone. Similarly, where the precursor material is water, the material treatment module 40 may oxidize water to produce a treated material that includes oxygen and ozone. Where the precursor material is an aqueous salt solution, the material treatment module 40 may oxidize the ions in the solution to create a beneficial or therapeutic agent dissolved in the solution or emitted as a gas. For example, chloride ions in a precursor material may, after interaction with the material treatment module 40, become chlorine gas under the reaction:

$$2Cl^- \rightarrow Cl_2 + 2e^- \quad (1)$$

which can then be expelled from the device into a desired location to apply its beneficial effects. Similarly, bromide ions may become bromine under the reaction:

$$2Br^- \rightarrow Br_2 + 2e^- \quad (2)$$

Conversely, the material treatment module may be able to reduce the precursor material to form the beneficial or therapeutic treated material.

It will be appreciated that the original or precursor material may be treated by the material treatment module 40 to alter a variety of characteristics of the precursor material, including without limitation, the concentration of a particular element such as oxygen, the pH of the material, the temperature of the material, the viscosity of the material, and the like. The material treatment module 40 is able to take a benign material that is easy to store, and create a reactive material that has therapeutic value. Furthermore, treating the material may be accomplished by a variety of methods, including without limitation, reducing the material, oxidizing the material, electrochemically altering the material, chemically altering the material, thermally altering the material, or using light to alter the material. It will be appreciated that the treated material may be a beneficial agent with various properties, characteristics, or attributes that may be therapeutic to a user. The apparatus 10 allows for transportable, single or multiple point-of-use application of the beneficial agent.

As will be discussed in greater detail below in connection with FIG. 2, the apparatus 10 may also have means for controlling the liquid treating module 40. For example, the device 20 may have an on/off switch 42 or other regulators. Additionally, the apparatus 10 may include visible and/or audible displays or indicators 44 to help the user determine a status of the liquid treating module. For example, the apparatus 10 may indicate when the apparatus is treating material or when it has stopped treating material. It may also indicate whether treated material is in the chamber 14.

The housing 12 may have an outlet 46 in material communication with the chamber 14 for releasing the treated material from the housing 12. In one embodiment, the outlet 46 is a port configured in the second end 26 of the barrel 18. The outlet 46 may be configured to receive a needle 48. For example, the outlet 46 may allow a needle 48 to be press fit into the outlet 46. The outlet 46 may also be threaded to receive a threaded end to the needle 48. The needle 48 may be attached to the outlet 46 by a Luer or other mechanical connection or fitting. It will be appreciated by those of skill in the art that the outlet 46 and needle 48 may be configured in a variety of ways in order to communicate with each other. The needle is in material communication with the outlet and thus, the chamber allows treated material to enter into the body and a specific site that will provide the most therapeutic value to the user.

The apparatus 10 may also include a valve 50 to help control the movement of material between the chamber 14 and the needle 48. In one embodiment, the valve is a stopcock valve. The valve may be positioned in closed state while material is being treated to prevent leakage of the material. Once a predetermined amount of material is treated, the valve may be positioned in an open state to allow the treated material to exit the apparatus 10.

Figure 2:
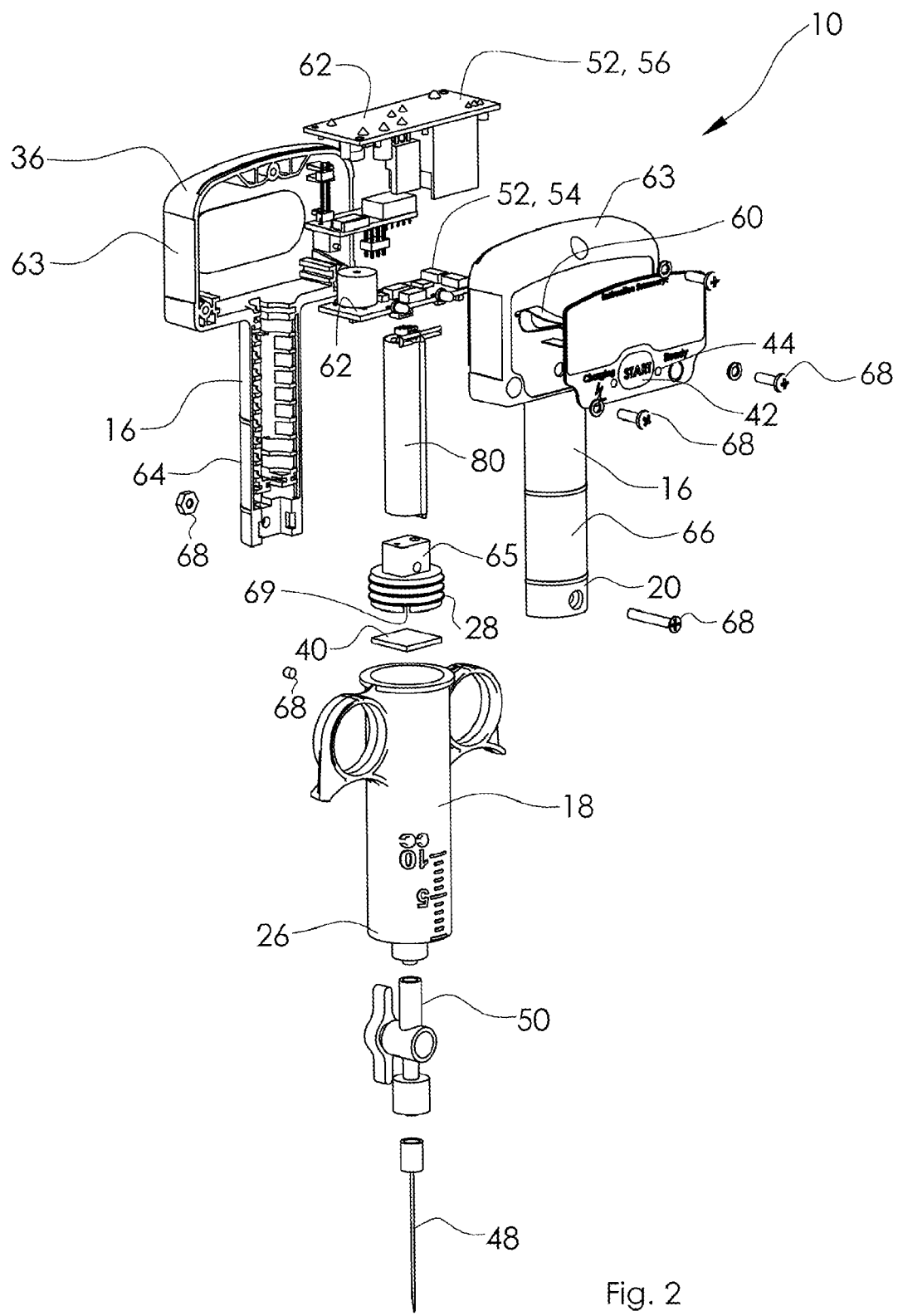
FIG. 2 is an exploded perspective view of the apparatus shown in FIG. 1.

Referring now to FIG. 2, a perspective exploded view of the embodiment of FIG. 1 of the present invention is shown. The apparatus 10 may further include a controller 52 for controlling the amount of material treated by the material treatment module 40. The controller 52 in one embodiment may include a timing circuit 54 for controlling the length of time the material treatment module 40 is permitted to treat material. In embodiments where the material treatment module 40 is an ozone generator and the precursor material is oxygen or air, the controller 52 may include an ozone circuit 56 for controlling the generation of ozone. The controller 52 is in electrical communication with the material treatment module 40. In one embodiment, the controller 52 is positioned within the plunger housing 53 and is used for controlling the amount of ozone generated by the material treatment module 40 which may be an ozone generator. It will be appreciated by those of skill in the art that the controller 52 may also include a relay circuit (not shown) in order for the controller 52 to properly control the function of the material treatment module 40.

A power source 80 is in electrical communication with the material treatment module 40 and the controller 52. The power source 80 can be direct current or alternating current. In one embodiment, the power source 80 includes a battery or a series of batteries positioned coaxially within the plunger 16. The controller 52 may include electronics capable of generating and delivering a high-voltage, high-frequency electrical signal to the material treatment module 40. The frequency of the signal can be between about one tenth of a kilohertz ("kHz") and about one thousand kHz. In one embodiment, the frequency is between about twenty kHz and about sixty kHz. The voltage of the electrical signal is between about one kilovolt and about twenty kilovolts. In one embodiment, the electrical signal is between about three kilovolts and about six kilovolts. In another embodiment, the power supply 80 can also supply an electric current with a voltage between about one volt and about thirty volts.

A switch 42 may be used to control the delivery of power by the power source 80. The switch and other electrical components communicate with each other electronically through wires or cables 60. When switch 42 is in the "on" position current is delivered to material treatment module 40, and when switch 42 is in the "off" position, no current is delivered. The switch 42 may be any number of electrical switches known in the art. For example, the switch may be a toggle that allows a user to complete or break the circuit multiple times. In one embodiment, the switch is a pull tab configured such that when the pull tab is pulled out of the apparatus 10, the circuit is complete and current is delivered to the material treatment module 40. The timing circuit 54 may automatically stop the generation or delivery of current at a predetermined time. The controller 52 or individual components 54 and 56 of the controller 52 may also include a buzzer or light source to provide an audible or visual signal or display to indicate whether the apparatus 10 is on or off, or status of the material treatment module 40. The apparatus 10 may include a display. It will be appreciated by those of skill in the art that the electronic components of the apparatus 40 may be hardwired to a circuit board 62 as shown, or may be controlled by a programmable microprocessor (not shown).

The control elements and other electronics are contained with the handle 36 and body of the plunger 16. The plunger 16 may include a plunger housing 62 having a first part 64 and a second part 66. The housing 62 parts 64 and 66 together form a hollow interior in which the controller 52 and power source 80 are housed. An end cap 65 may be configured at the first end 20 of the plunger 16 to help hold the interior components in place. The end cap 65 may be configured with a seal 28 to provide sealing engagement with the interior of the barrel 18. The end cap 65 may also be configured to help control the telescoping engagement of the plunger 16 within the barrel 18. The plunger housing parts 64 and 66 may be secured together by fastening hardware 68 known in the art such as nuts, bolts, washers, set screws, and the like. The housing halves of the plunger 16 and other parts of the apparatus 10 such as the barrel 18 may be made of molded plastic and attached together in their operational state. The attachment may be accomplished in a number of ways including without limitation, adhesion or other types of bonding, welding, crimping, ultrasonic coupling, thermal coupling, and the like. The housings halves may also be configured to matingly engage each other by press fitting, snap fitting, and the like. Fasteners 68 of all types known in the art may also be used. It will be appreciated by those of skill in the art that the individual components may be made and combined in a variety of ways to practice the teachings of the invention. In one embodiment, the electronics and control components may be located in the barrel 18. In another embodiment, the electronics and control components may be located in a separate housing or module from the plunger 16 or barrel 18.

The plunger 16 and barrel 18 may be made from any suitable material that is substantially rigid, such as glass, stainless steel, polycarbonate, high density polyethylene, chlorinated polyvinylchloride, silicone, ethylene-propylene terpolymer, and fluoropolymer materials, such as polytetrafluoroethylene, fluorinated ethylene-propylene, and the like. It will be appreciated by those of skill in the art that the material used to make the apparatus 10 should be capable of functioning properly in light of the particular type of material treatment being accomplished by the material treatment module 40. For example, where the material treatment module 40 is an ozone generator, the plunger 16, barrel 18, and other components in contact with the material should be made of an inert material such as those listed above when exposed to ozone. When the material is being treated by heat, the material should be able to withstand the range of heat being used. Similarly, when the precursor material is being treated by ultraviolet light, the housing must be compatible to ultraviolet light.

The material treatment module 40 may be positioned within the end 20 of the plunger 16. In one embodiment, the material treatment module 40 is an electrochemical cell 40 having a cathode 70, anode 72, and an electrolyte (see FIG. 3). The chip 40 may be positioned within a cavity 69 configured within plunger 16. The material treatment module 40 is coaxial with the plunger and is open to and in communication with the chamber 14 defined by the first end 20 of the plunger 16 and the second end 26 of the barrel 18. Furthermore, it is to be understood that the material treatment module 40 may be disposed at any suitable position relative to the housing 12 of the apparatus 10. When the housing 12 is in the form of plunger 16/barrel 18 combination, the material treatment module 40 may be disposed at any suitable location between the first end 20 and the second end 22 of the plunger 16, or at any location between the first end 24 and the second end 26 of the interior of the barrel 18. In addition, the material treatment module 40 may also be disposed at any suitable location on an exterior surface of the device 10, or at a location outside the device where the material treatment module 40 is unattached to, but connected to, the device.

The material treatment device 40 may also be a corona discharge device. The material treatment module 40 may also be an ultraviolet ("UV") light source. In these embodiments, the power source 80, and electronic circuits 54, 56, circuit boards 62, cables 60 and controller 52 would be modified to allow for the proper function of the corona discharge device or UV light source. For example, for the UV light source device, the electronics would need to provide a wavelength of the light between about 100 nm and about 700 nm or between about 140 nm and about 200 nm.

In other aspects, the material treatment module 40 may be an open vessel for storing an ozonated gel and a heating element, such that activation of the heating element elevates a temperature of the gel causing desorption of ozone-oxygen mixture from the gel. The gel can be formed by sparging ozone through olive oil and then chilling the olive oil. The olive oil is chilled to a temperature of between about minus fifteen ° C. and about ten ° C. It will be appreciated by those of skill in the art that a variety of material treatment module 40 options may be used alone or in combination to practice the teachings of this invention.

A needle 48 attached to the outlet 46 may be of any desired material, length or gauge that may be desired according to the treated material being delivered. In one embodiment, the treated material is an oxygen-ozone mixture of therapeutic value, the details of which will be discussed in greater detail below. Where an oxygen-ozone mixture is being delivered into a herniated disc, the needle 48 can be a Chiba needle or Franceen needle or other suitable needle as will occur to those of skill in the art.

Figure 3:
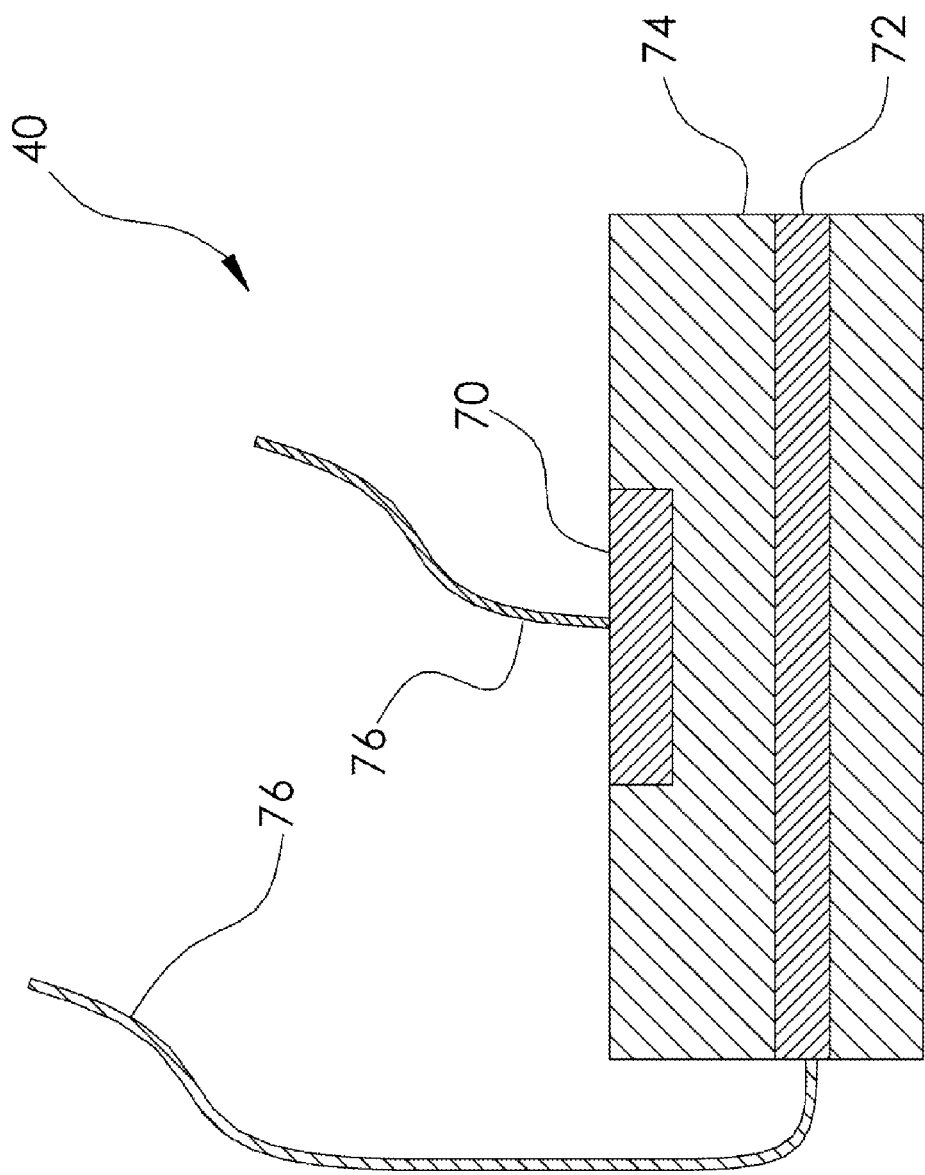
FIG. 3 is side cross-sectional view of the material treatment module of FIG. 1.

Referring now to FIG. 3, a more detailed view of a material treatment module 40 according to the present invention is shown. The material treatment module 40 may be an electrochemical cell comprising a cathode 70, an anode 72, and an electrolyte 74. At least a portion of the electrolyte 74 is positioned between the cathode 70 and the anode 72. The power source (not shown) provides voltage across the cathode 70 and the anode 72 by means of wires 76. In this embodiment, the material treatment module 40 can be an electrochemical ozone generator. An oxygen or air precursor material may interact with the material treatment module 40 such that an oxygen-ozone mixture is created. This mixture may be released from the electrochemical cell configuration of the material treatment module 40 by the electrolysis of water and the production of ozone and oxygen at the anode 72. In one embodiment, an electric current is used with an applied voltage between about three volts and about twenty volts. In another embodiment, a voltage between about two volts and about ten volts is used.

Figure 4:
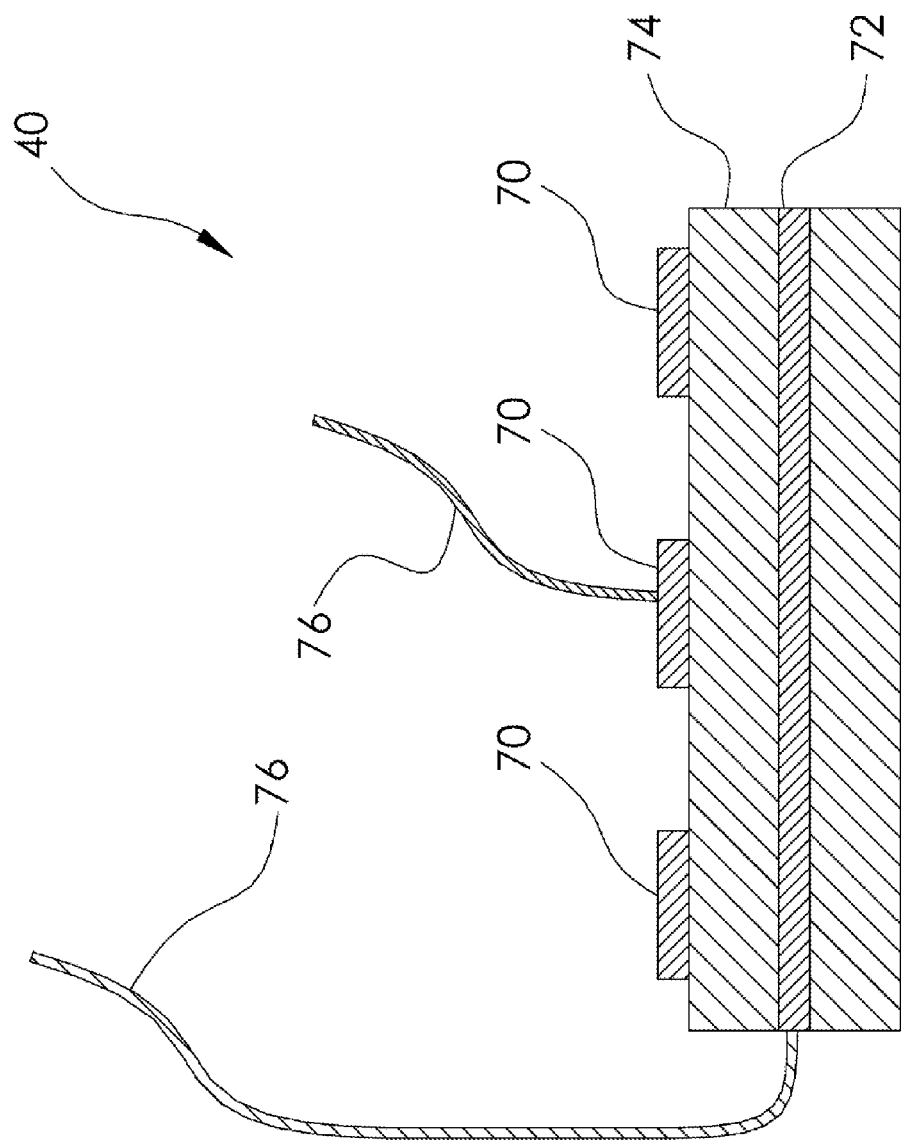
FIG. 4 is side cross-sectional view of another embodiment of the material treatment module of FIG. 1.

Referring now to FIG. 4 another embodiment of the material treatment generator 40 is illustrated. The material treating module 40 may be a surface-discharge corona. In this embodiment, a dielectric material 174 may be positioned between a pair of electrodes 170 and 172. Wires 176 may be used to connect to a discharge electrode 170 and an induction electrode 172. The electrodes are incorporated within a high purity alumina or silica dielectric 174. In one embodiment, the electrodes 170 and 172 contain without limitation, tungsten, platinum, nichrome, stainless steel or combination thereof. When a high-frequency, high-voltage power source is applied between the two electrodes 170 and 172, a stable high-frequency surface corona discharge takes place on the discharge electrode 170. An alternative embodiment utilizes a more traditional gap-discharge, corona material treatment module 40 that utilizes a glass dielectric and low-frequency high voltage power. In this configuration, the device 10 is used to create treated gas in the form of oxidizing gas. For example, the chamber 14 (see FIG. 1) may contain a starting gas in the form of pure oxygen gas. An oxygen-ozone mixture is released from the corona discharge device 40 by passing the oxygen-containing gas through an electrical field originating from device 40 at a frequency between about one-tenth kilohertz ("kHz") and about one thousand kHz. In one embodiment, a frequency between about twenty kHz and about sixty kHz is used. An electric current with a voltage between about one kilovolt and about twenty kilovolts and a more presently preferred voltage between about three kilovolts and about six kilovolts may also be used.

Figures 5A, 5B:
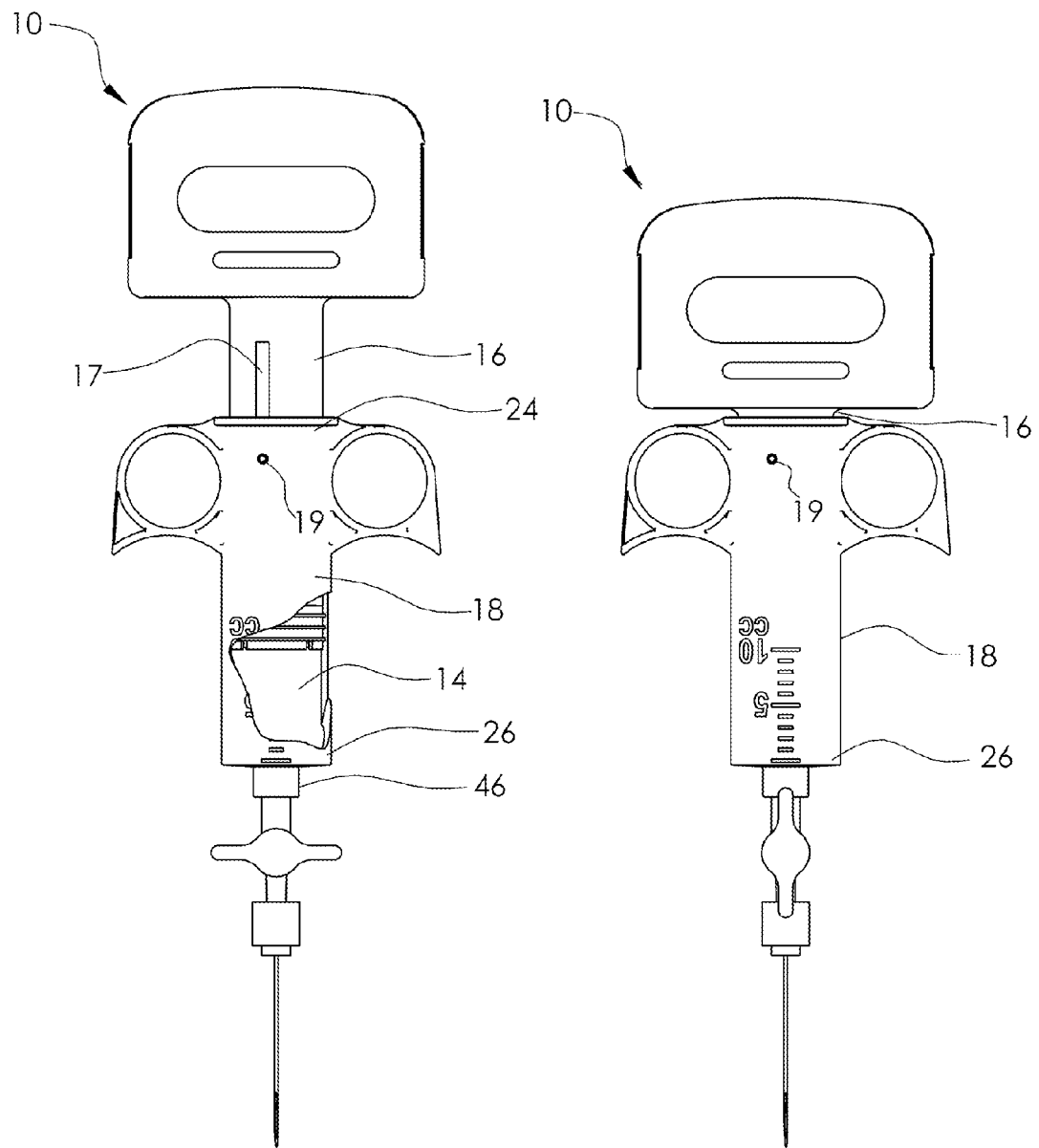
FIG. 5a is a plan view of the apparatus shown in FIG. 1 in a fill position.
FIG. 5b is a plan view of the apparatus shown in FIG. 5a in a dispensing position.

Referring now to FIGS. 5a and 5b, a device 10 according to the present invention is illustrated. In FIG. 5a, the device 10 is shown in a fill position where the first end 20 of the plunger 16 is retracted to fill the barrel 18. FIG. 5b shows the device 10 in a dispensing position, where the first end 20 of the plunger 16 is substantially within the barrel 18 such that the first end 20 of the plunger 16 is adjacent the second end 26 of the barrel 18. The range of motion of the plunger 16 within the barrel 18, between the fill position and the dispensing position, may be defined by a groove 17 configured within the plunger 16. A stop 19 configured within the barrel 18 may be positioned within the groove 17 to control the maximum fill volume of the barrel 18. In another embodiment, multiple stops 19 can be incorporated to control both the fill and delivery volumes of the barrel 18. It will be appreciated by those of skill in the art that movement of the plunger 16 within the barrel 18 may be accomplished in a variety of ways known in the art. As stated above in connection with FIG. 1 the first end 20 of the plunger 16 and the second 26 of the barrel 18 form a chamber 14 or an accumulator. The chamber 14 volume decreases as the plunger is moved from a fill position to a dispensing position.

In use, the device 10 may be in a position such that the chamber (seen best in FIG. 1) is capable of holding a predetermined amount of material. This precursor material, as referred throughout the specification, may be any volume of material to be treated by the device. In most embodiments, it is a precursor liquid, gas, gel, or combination thereof that will be treated by the device in order to generate a beneficial or therapeutic agent. Precursor material may be drawn into the chamber 14 by attaching the outlet 46 or an apparatus attached the outlet 46 such as a needle to the source of precursor material and drawing the plunger 16 toward the fill position. Precursor material may also be charged into the chamber 14 from an external source attached to the device 10 or distant from the device 10. Precursor material may be charged into the chamber 14 before packaging of the device or after the user has obtained the device 10. It will be appreciated by those of skill in the art that there are a number of ways to charge the device 10 or chamber 14 with precursor material.

The precursor material may include, without limitation, air, oxygen, water, nitrogen, carbon dioxide, chlorine, bromine, and combinations thereof. It may also include a salt solution, either alone or in combination with the foregoing. For example, the salt solution may include NaI, NaF, NaCl, NaBr, and the like. In one embodiment, the precursor material comprises a salt consisting of one or more monovalent or divalent cations including without limitation at least the following cations: $H^+$, $Li^+$, $Na^+$, $K^+$, $NH_4^+$, $Ca^{++}$, $Mg^{++}$, $Sr^{++}$, $Ba^{++}$, and combinations thereof. In another embodiment, the precursor material comprises a salt consisting of one or more monovalent or divalent anions, including without limitation: $F^-$, $Cl^-$, $Br^-$, $I^-$, $SO_4^{2-}$, $NO_3^{2-}$, $CO_3^{2-}$, $O^{2-}$, $S^{2-} CH_3COO^-$ (acetate) and combinations thereof.

The precursor material may be in the form of a gas, liquid, gel, solid or combinations thereof. For example, the precursor material could be salt or ice or other solid forms. In one embodiment, the precursor material is a solid in the form of particles suspended in a fluid or gel. It will be appreciated that where the treated material is recycled for further treatment or further generation of therapeutic or beneficial agent, or where it is desirous to treat a material twice in order to generate a higher concentration of some beneficial agent, then the precursor material may contain treated material. Thus, the probe and method of treating a tissue include a module and step for creating a beneficial material, or the constituent of a beneficial material which may become a beneficial material as part of a subsequent reaction.

The device 10 may then be activated by engaging a switch 42 (FIGS. 1 and 2), which allows activation of the power source 80 (FIG. 2), causing the material treatment module 40 to interact with the precursor material in the chamber 14. Depending upon the type of material treatment module 40 being used, activation of the device 10 creates or generates beneficial agent by treating the 0 material to create a treated material. For example, where the material treatment module 40 is an ozone generator in the form of a corona generator, and the precursor material is oxygen, activating the device 10 causes the material treatment module 40 to emit a field that interacts with the oxygen in the chamber 14 thereby creating ozone mixed with oxygen, which is a beneficial agent. Once the ozone generation cycle is complete, the plunger 16 is depressed to deliver ozone from the outlet 46. Of note, in the one embodiment the stroke of plunger 16 is chosen so that, when fully depressed, material treatment module 40 may come into close proximity of the second end 26 of the barrel 18, but without actually coming into contact therewith.

As used throughout the specification, treated material may be material that has been altered or modified in any way by operation of the device 10. Thus, the terms precursor material and treated material refer to material at different stages of a single operation of the device 10. Using the example above, where the precursor material is oxygen and the material treatment module 40 is an ozone generator, activation of the device 10 will create a treated material consisting of a mixture of ozone and oxygen. If this mixture were stored and later charged into the device for a second application, this treated mixture would then be the precursor material for the second application of the device 10.

The treated material is the therapeutic agent desired to be delivered to a patient. The treated material may include without limitation, ozone, oxygen, nitric oxide(s), chlorine, fluorine, chlorine dioxide, iodine, carbon dioxide, bromine, bromine dioxide, oxygen radicals; hydroxyl radicals; ionic oxygen; oxygen treated with energy and combinations thereof. At least a portion of the treated material may also include precursor material. The treated material may also include inert gases which can include, but are not limited to, nitrogen, helium, carbon dioxide, and/or combinations thereof.

Referring now to FIG. 6a, another embodiment of the device 310 is illustrated. The device 310 includes a plunger 316 and a barrel 318 that define a chamber 314 for holding precursor material. The plunger 316 has a first end 320 and a second end 322. The barrel 318 has a first end 324 that is open for receiving the first end 320 of the plunger 316 such that the plunger 316 movably engages the barrel 318. The barrel 318 also includes a second end 326. The second end 326 of the barrel 318 may be configured with an outlet 346 that serves as the outlet 346 for the chamber 314. A needle 348 may include a first end 382 and a second end 384. The second end 384 of the needle 348 may be attached to the outlet 346 using a Luer or other mechanical connection or fitting.

In this embodiment, the material treatment module 40 is within the needle 348 or is the needle 348 itself. As can best be seen in FIG. 6b, a cross sectional view of FIG. 6a taken along line A-A, and FIG. 7c, a blown up view of area B, the needle 348 utilizes a flow-through electrochemical cell to create treated material in the form of a therapeutic agent. The electrochemical cell needle 348 includes an anode 370 and a cathode 372. Electric current is delivered to the anode 370 and cathode 372 by wires 376 attached to a power source 380. The chamber 314 is charged with precursor material or precursor or electrolyte 374. As with other embodiments disclosed herein, the electrochemical reaction between the material treatment module 340 and the precursor material can be controlled by the selection of electrode or electrolyte material. The electrodes 370 and 372 affect the electrochemical kinetics of the electroxidation/electroreduction reaction at the electrode 370 and 372.

The power source is initiated to polarize the anode 370 and cathode 372 which generates therapeutic agent by electrooxidizing or electroreducing the precursor material as it is plunged out the chamber 314 and into the needle 348. In another embodiment, the anode 370 is the metallic wall of the needle. The anode 370 and cathode 372 may be reversed for all embodiments. As discussed above, the timing and control of the applied voltage and/or current power source control the amount of beneficial agent that is produced by the material treatment module 40, and may be manual or automatic (i.e. programmable microprocessor controlled).

It will be appreciated by those of skill in the art that for ease of operations, the wires can be conductors that are printed on the inside of the chamber 314. In one embodiment the wires 376 are insulated and the electrodes 370 and 372 are conductive and selective for the desired beneficial agent. For gas precursors, the electrodes 370 and 372 may be tungsten, platinum, stainless steel, nichrome, or aluminum configured in the needle 348. It will be appreciated that the material treatment module 40 in the needle 348 configuration may also be set up as corona discharge device in a manner similar to a traditional gap-discharge, corona discharge devices. In this configuration, the needle would be a gas treating module that utilize a glass dielectric on the high-voltage electrode and would be powered by low-frequency, high-voltage power. For liquid precursors, similar electrodes are used, however they are powered by low voltages, and do not require a dielectric like the high voltage electrodes.

Referring now to FIG. 7a, another embodiment of the device 410 according to the present invention is shown. The device 410 includes a plunger 416 and a barrel 418 that define a chamber 414 for holding precursor material. The plunger 416 has a first end 420 and a second end 422. The barrel 418 has a first end 424 that is open for receiving the first end 420 of the plunger 416 such that the plunger 416 movably engages the barrel 418. The barrel 418 also includes a second end 426. The second end 426 of the barrel 418 may be configured with an outlet 446 that serves as the outlet 446 for the chamber 414. A needle 448 may include a first end 482 and a second end 484. The second end 484 of the needle 448 may be attached to the outlet 446 using a Luer or other mechanical connection or fitting.

In this embodiment, the material treatment module 40 is the needle 448. As can best be seen in FIG. 7b, a cross sectional view of FIG. 7a taken along line A-A, and FIG. 7c, a magnified view of area B, the needle 448 utilizes a flow-through electrochemical cell to create treated material in the form of a therapeutic agent. The electrochemical cell needle 448 includes an anode 470 and a cathode 472. Electric current is delivered to the anode 470 and cathode 472 by wires 476 attached to a power source 480. The chamber 414 is charged with precursor material or precursor or electrolyte 374.

In this embodiment, the needle 448 houses electrodes 470 and 472 that are used to produce a beneficial agent in situ, or in other words, within the body. In this embodiment, additional electrolyte may or may not be supplied in chamber 414. The electrodes 470 and 472 extend beyond the opening 486 to have greater access to body fluid for generating in situ treated material which can be a beneficial agent. It will be appreciated that the plunger 416/barrel 418 configuration is not necessary for this application because the treated material is generated beyond the end 486 of the needle 448. However, the syringe-type configuration may be desirable to provide additional saline solution or other liquid precursors by plunging of the plunger 416 into the barrel 418 for patients that are dehydrated or to areas of the body that don't have much material. The first end 482 of the needle may have a protective shield or shroud (not shown) that protects the electrodes 470 and 472 from being damaged upon insertion.

FIG. 8a is a diagrammatic sectional view of an electrochemical probe 512 in accordance with an embodiment of the present invention. The electrochemical probe 512 has a needle 515 that is shown supported in a handle 518. The handle 518 simulates a syringe with a thumb plate 521 and a pair of opposite finger engaging grips 524, 525 to facilitate manipulation. Although (not shown in FIG. 8a), the handle 518 may include a syringe for additionally supplying a precursor material and/or a beneficial agent, as described above. Alternatively, the handle 518 could be replaced by any of the devices 10, 310, and 410 described with regard to the embodiments of FIGS. 1-7c above. As such, the needle 515 could be supported in fluid communication with any of the outlets 46, 346, and 446. A power source 528, which may include a battery or other DC output, is shown supported in the handle 518. The handle 518 may further have electronics for controlling functions of the probe 512 similar to the electronics described above with regard to the devices of FIGS. 1-7c.

The needle 515 shown in the embodiment of FIG. 8a has a first end 531 with a head 534 for connection with the handle 518 by a Luer or other connection mechanism. The handle 518 may have a socket 529 that receives the needle in a friction fit, threaded engagement, or other connection mechanism. Alternatively, the head 534 may serve as a handle when the probe is manipulated without the handle 518. In any case, first and second lines or wires 537, 538 may be insulated wires that extend from the power source 528 or a separate power source to the needle. The first wire 527 connects one terminal of the power source to the needle to provide a first electrode of a pair of electrodes. The second wire 538 connects another terminal of the power source to a second electrode 541. The second electrode 541 is insulated from the first electrode (needle 515) by one or more insulators 544. As shown, the second electrode 541 is disposed in a hollow interior of the needle 515, and the insulators 544 have through openings 547 that receive and space the second electrode from an inner walls of the needle 515.

The needle 515 has a second end 550 that includes a tip 553. In the embodiment of FIG. 8a, a material treatment module 556 is located in the tip 553. The material treatment module 556 is adapted to facilitate placement of an electrolyte between the first electrode (needle 515) and the second electrode 541. The material treatment module may be charged with a precursor by any of a number of mechanisms. For example, the needle 515 may be dipped to draw a fluid into the tip 553 by capillary action. Alternatively or additionally, an absorbent membrane or material 559 may be placed between the first and second electrodes 515, 541 to help draw the precursor material into the material treatment module 556. Other mechanisms may include suction provided by a plunger in order to draw the precursor material in through the tip 553. Alternatively, a precursor material may be fed under pressure or gravity through the first end 531 similar to the precursor materials described with regard to the embodiments set forth above.

FIG. 8b is a diagrammatic cross sectional view taken along section A-A of FIG. 8a. The absorbent material 559 may take any of a variety of forms. However, in FIG. 8b, the absorbent material is shown bent and supported in a friction or resiliently bent fitting relationship between the first and second electrodes 515, 541. Other configurations could be implemented without limitation. For example, the second electrode could be centered within the needle 515 and the absorbent material could form a tubular wick that spans a gap between substantially an entire circumference of each of the first and second electrodes 515, 541.

In one embodiment, the electrolyte is fluid. The fluid may be water from within the tissue or from a source outside the tissue. The water is split to form hydrogen gas and oxygen gas. In the case where the first electrode 515 is the cathode, hydrogen is formed at an interface of the absorbent material 559 and the first electrode 515. Oxygen and ozone gases are formed at the anode at an interface between the absorbent material 559 and the second electrode 541. Alternatively, if the first electrode 515 is the anode, the oxygen and ozone gases are permitted to escape out a main opening 562 and auxiliary openings 565 through a sidewall of the needle 515 and into a target tissue. In this configuration, with the second electrode as the cathode, the hydrogen gas can escape axially toward the first end 531 of the needle 515 and through openings 568 in the insulators 544. Additional openings similar to auxiliary openings 565 may be provided along a length of the needle 515 to facilitate escape of the hydrogen gas. The electrolyte may also be an organic solvent such as methanol, ethanol, isoproponal, or other alcohols, glycols, and the like.

FIG. 9a is a diagrammatic sectional view of an electrochemical probe 571 in accordance with another embodiment of the present invention. The probe 571 may include a needle 574 and the handle 518. Alternatively, the needle 574 could be utilized with another handle or no handle, as described with regard to FIG. 8a above. The handle 518 has the thumb plate 521 and finger grips 524, 525. The handle 518 may house the power source 528 and any electronics. The handle 518 may form the socket 529 for receiving a head 534 of the needle 574. The handle may include a syringe with a plunger and barrel, or may serve primarily as a handle for facilitating manipulation of the probe 571 during use.

The needle 574 of FIG. 9a differs from the needle 515 of FIGS. 8a and 8b in that the needle 574 is not one of the electrodes. Rather, the needle 574 of FIG. 9a has a first electrode 577 and a second electrode 578 that are both disposed on an interior of the needle 574. Wires 537, 538 connect respective terminals of the power source 528 to the first and second electrodes 577, 578. One or more insulators 581 receive the first and second electrodes 577, 578 and inhibit them from contacting each other and an inner wall of the needle 574. Structurally the needle 574 may be substantially the same as the needle 515 described above. Alternatively, the needle 574 may have structural differences to accommodate the first and second electrodes 577, 578. The insulators 581 may be similar to the insulators shown and described with regard to FIG. 8a. As shown, the insulators 581 have passageways 584 that permit the escape of gases axially along a length of the needle 574.

As shown in FIG. 9a, the needle 574 may have the first end 531 and the second end 550 that are functionally and structurally similar to those described in the same terms with regard to FIG. 8a. The second end 550 may include a tip 587 that is configured differently by virtue of the placement of the first and second electrodes 577, 578 therein. However, the tip 587 of FIG. 9a may have the primary opening 562 out through an axial end and auxiliary openings 590 similar to those of FIG. 8a.

As with the needle 515 of FIG. 8a, the needle tip 587 of FIG. 9a houses a material treatment module 593 that can be charged with an electrolyte in any number of ways. An absorbent membrane or material 596 may be placed between the first and second electrodes 577, 578 to help retain the electrolyte and to provide increased surface area over which electrolysis may take place at an interface between the absorbent material 596 and the electrodes 577, 578. Thus, the absorbent membrane or material 596 that forms the interface facilitates and/or enhances electrolysis for at least some electrolytes and some electrochemical reactions.

FIG. 9b is a diagrammatic cross sectional view taken along section A-A of FIG. 9a. As shown, the absorbent material 596 may have a friction fit or a resilient fit by virtue of the resiliency of the membrane or material 596, and thus is retained between the first and second electrodes 577, 578 such that the absorbent material does not inadvertently fall out of the material treatment module 593. Also, the electrodes 577, 578 may have a flat configuration that provides a larger interface with the absorbent material 596 and/or electrolyte than would rod electrodes.

While the electrodes 577, 578 have been shown as separate elements disposed on an interior of the needle 574, it is to be understood that one or both of the electrodes could be disposed exteriorly of the needle 574 and/or may be integrated with structure of the needle. For example, the electrodes could be printed onto the inner and/or outer surface(s) of the needle 574. The electrodes in this case could be insulated from each other by insulator layers or by providing the needle itself of an insulator material. In either embodiment, an insulator material within the needle or the needle itself an insulator material, the insulator material insulates the electrical conductor from the needle. The electrochemical probe may include a channel within the insulator material. A channel may also be located within the needle. The channels serve to permit passage of electrolysis products through the needle and/or insulator material and out of the electrochemical probe. The needle may also include a plurality of apertures to allow a fluid to communicate with the tissue and the needle.

FIG. 10a is a diagrammatic sectional view of an electrochemical probe 602 in accordance with another embodiment of the present invention with similar elements labeled similarly to the embodiments described above. For example, the handle 518 with its thumb plate 521 and finger grips 524, 525 may be the same as those of FIGS. 8a and 9a. The power source 528 may be similarly housed in the handle 518. However, the lines or wires 537, 538 may be longer and extend along most of the length of a needle 605. The needle 605 is configured differently from the needles of the embodiments of FIGS. 8a and 9a. In the embodiment of FIG. 10a, first and second electrodes 608, 609 are located and supported on a substrate 612 that may be integral with the needle 605. Alternatively, the substrate 612 may be formed separately and mounted in a tip 615 at a second end 618 of the needle 605. In this way, the substrate 612 may help to form a material treatment module 618. One or more openings (not shown) similar to openings through the insulators described above may be formed through the substrate 612 to facilitate escape of gases and/or liquids during electrolysis. These openings may be placed to selectively encourage escape of one electrochemical product while causing accumulation of another electrochemical product in the material treatment module 618. A treated material such as a gas may be delivered to a target tissue through the primary opening 562 or auxiliary openings

621. An absorbent membrane or material 624 may be placed between the electrodes 608, 609 similarly to the embodiments described above.

FIG. 10*b* is a diagrammatic cross sectional view taken along section A-A of FIG. 10*a*. The absorbent material 624 may be retained between the electrodes 608, 609 by a friction fit or by the resiliency of the material of the absorbent membrane or material 624. The electrolysis is facilitated similarly to the embodiments described above.

FIG. 11*a* is a partial diagrammatic sectional view of a portion (corresponding to an alternative embodiment for region B outlined by a dashed line in FIG. 10*a*) of an electrochemical probe in accordance with another embodiment of the present invention. In the embodiment of FIG. 11*a*, a needle 627 supports a substrate 630 at or near a distal end 633 of the needle 627. Thus, a material treatment module becomes very small or does not exist in this embodiment. Rather, in the embodiment of FIG. 11*a*, first and second electrodes 636, 637 are supported in the substrate 630. The substrate 630 has a face at or near the distal end 633, and the electrodes 636, 637 protrude only slightly from the face and the needle 627. In this configuration, the electrolysis is caused to occur substantially within a target tissue itself. Otherwise, the embodiment of FIG. 11*a* may be similar to the embodiment of FIG. 10*a*.

FIG. 11*b* is a diagrammatic cross sectional view taken along section A-A of FIG. 11*a*. Thus, the electrodes 636, 637 are shown in spaced relation without any absorbent material disposed between them.

FIGS. 12*a*-12*c* are diagrammatic cross sectional views of further alternative embodiments that may be substituted for any of the embodiments shown in FIGS. 8*a*-11*b*. Any of a variety of configurations for the electrodes may be implemented. For example, FIG. 12*a* shows a first tubular electrode 640 and a second rod electrode 641 with the rod electrode 641 disposed concentrically inside the tubular electrode 640. An absorbent material 644 may be formed in a tubular configuration to facilitate retention of an electrolyte between the electrodes 640, 641. FIG. 12*b* shows a configuration with an arcuate outer first electrode 647 and an inner rod second electrode 648. FIG. 12*c* shows a rectangular needle 651 having a U-channel first electrode 654 and a flat plate second electrode 655. Any of these configurations may accommodate absorbent membranes or materials. The configurations shown in FIGS. 12*a*-12*c* may be applied all or in part in any combination to the embodiments of FIGS. 8*a*-11*b* without limitation.

Although certain functionality is described herein with respect to each of the operations of the method of delivering a beneficial agent to a tissue, other embodiments of the method may implement similar functionality using fewer or more operations. Additionally, some embodiments of the method may implement more or less functionality than is described herein. The method may be implemented with other systems that may have components that are different from those described herein. Therefore, the description of the embodiment of the method below is an example, and the described elements need not correspond to those described with regard to the systems and apparatuses above.

With regard to use of the apparatuses of FIGS. 1-7*c* and similar devices, a method of dispensing a material using a handheld dispensing apparatus is disclosed. A dispensing apparatus or device 10, 310, 410, as discussed above may be used to dispense the material. The method includes collecting a precursor material in the chamber 14, 314, 414. The material treatment module 40, 340, 440 is activated. The precursor material collected in the chamber 14, 314, 414 is treated by the material treatment module to create a treated material. The needle 48, 348, 448 is positioned within a body. The treated material is then dispensed out of the device 10, 310, 410 or chamber into the body through the needle. A method for using the probes 512, 571, and 602 of the embodiments of FIGS. 8*a*-12*c* may be substantially similar except for an operation of collecting may be omitted.

In one embodiment, the precursor material may include, without limitation, air, oxygen, water, nitrogen, carbon dioxide, chlorine, bromine, iodine, flourine and combinations thereof. It may also include a salt solution, either alone or in combination with the foregoing. For example, the salt solution may include NaI, NaF, NaCl, NaBr, and the like. The salt may also be formed of at least one monovalent or divalent cations including without limitation, cations of $H^+$, $Li^+$, $Na^+$, $K^+$, $NH_4^+$, $Ca^{++}$, $Mg^{++}$, $Sr^{++}$, $Ba^{++}$, and combinations thereof. In another embodiment, the precursor material comprises a salt consisting of at least one monovalent or divalent anions, including without limitation, $F^-$, $Cl^-$, $Br^-$, $I^-$, $SO_4^{2-}$, $NO_3^{2-}$, $CO_3^{2-}$, $O^{2-}$, $S^{2-}CH_3COO^-$ (acetate) and combinations thereof.

It will be appreciated by those of skill in the art that the term salt solution includes compounds formed when the hydrogen of an acid is replaced by a metal.

In some embodiments, the method includes applying a low frequency voltage to a pair of electrodes. For this disclosure, low frequency refers to frequencies in a range from zero to two hundred kHz inclusive. Low frequency is considered to include DC voltages. The optimal frequency is driven by the resistance-capacitance (R-C) time constants of the electrochemical probe and the waveform type. In some embodiments, the frequency is between 0.05 and 5 kHz. Waveform types may be simple unipolar square, triangular, sine or more complex bipolar waveforms. The method also includes causing in situ electrolysis within a tissue in a body by applying the low frequency voltage to the pair of electrodes. Some embodiments of the method include placing an absorbent membrane 559, 596, 624 between the electrodes to help retain electrolyte in this position.

In accordance with some embodiments of the method, a beneficial effect is imparted to the tissue by forming at least one of oxygen, ozone, and oxygen ions. Alternatively or additionally, embodiments of the method may include causing at least one of electro-oxidation and electro-reduction of a material of the target tissue. This electro-oxidation and electro-reduction may be the direct result of causing the in situ electrolysis. Alternatively, the oxidation or reduction may be caused indirectly by products of the electrolysis. In accordance with some embodiments, causing in situ electrolysis of the material of the tissue includes causing at least one of electro-oxidation and electro-reduction of proteoglycans or any other component of the tissue. The oxidation and/or reduction of components of the target tissue can have the effect of creating gases or other products that are more easily dissipated or otherwise removed from the target tissue. This can have the benefit of reducing a volume and an associated pressure in an inflamed region associated with the target tissue.

In some of the embodiments of the method, the absorbent membrane or material 559, 596, 624 is at least partially filled with fluid from the target tissue such as water. Some tissues tend to give up moisture more readily than others. Therefore, in some applications, the tissue may need to be ablated prior to filling the absorbent membrane 559, 596, 624. Higher voltages and/or high frequency voltages may be implemented as described above for ablating tissue for the purpose of facilitating extraction of water. Alternatively, the absorbent membranes 559, 596, 624 may be filled, at least in part, with fluid from a source external to the tissue. That is, water from outside the body or from another part of the body may be supplied for water splitting in the material treatment modules 556, 593, 618 and/or in the target tissue itself. The absorbent membranes 559, 596, 624 may also be filled, at least in part, with a organic solvent such as methanol, ethanol, isopropanol, or other alcohols, glycols, and the like.

In some embodiments, applying a low frequency voltage includes applying a voltage in a range from one to thirty volts. In other embodiments, the method includes applying a voltage in a range from one to six volts. In still other embodiments, the method includes applying a low frequency voltage in a range from six to twelve volts. It is to be understood that the voltages for dehydrating and for causing oxidation/reduction may be low frequency or DC voltages without limitation. For example, applying a low frequency voltage may include applying a voltage having a frequency in a range from greater than or equal to 0 kHz to 200 kHz. In some embodiments a low frequency voltage is applied at a range between about 0 kHz and about 50 kHz. In some embodiments the frequency range is between about 0.05 kHz and about 5 kHz inclusive. In other embodiments, the frequency ranges between 0.1 kHz and 1 kHz inclusive.

For the embodiments of FIG. 1-7c, activating the material treatment module 40 includes engaging a switch to allow power from a power source to be delivered to the material treatment module. The method may also include deactivating the material treatment module, either manually or automatically. The method may also include detecting an amount of material treated by the material treatment module to determine when to shut off the module 40 or device 10. This may be accomplished by monitoring a display. Similar activation may be accomplished by engaging a switch (not shown) for the probes 512, 571, and 602 of FIGS. 8a-12c. Similar monitoring may also be implemented with the probes 512, 571, and 602. Furthermore, one or more sensors 658, 659 may be placed at interfaces between the electrodes and the electrolyte for detecting an amount of treated material. For example, an ozone and or oxygen sensor may be used to detect and send signals for analysis of weight percentages in electronics of the probes. The sensors may be placed at other locations without limitation.

In the application involving water splitting, these parameters may be varied to control the generation of oxygen, ozone, and/or ions of oxygen. As mentioned above, the percentage of ozone can also be monitored by one or more sensors 658, 659 at or near the anode, for example. The sensors 658, 659 may be coupled to or include an analyzer that determines weight percent. The pressure may be measured by a pressure sensor or barometer. One or more temperature measuring devices may take the form of wire thermocouples, thin or thick film thermocouples, resistors, a resistance temperature detector (RTD), or another type of temperature measurement device. Signals from the sensors or measurement devices may be connected with an electronic controller that utilizes predetermined logic in circuitry or in computer readable media to adjust the voltage or some other parameter in order to control the ozone generation level.

In embodiments, where the housing is a syringe configuration with a plunger 16, 316, 416 movably engaged within a barrel 18, 318, 418, dispensing the material may include moving the plunger relative to the barrel such that treated material is delivered through the needle into the body.

While many of the described embodiments are adapted to cause electrolysis in situ in a tissue, the effects of the electrolysis may vary among the different embodiments and with adjustments that are made during use. Additionally, some embodiments of a system and apparatus may include all or part of the apparatuses described herein, and may further include other components. Similarly, embodiments of the method may utilize any combination of elements among the devices and probes described. For example, depending on the level of automation and portability of a given embodiment, a controller, computer readable media, and/or a separate power source may or may not be included.

Reference throughout this specification to "one embodiment," "an embodiment," or similar language means that the described feature, operation, structure, or characteristic may be implemented in at least one embodiment. Thus, the phrases "in one embodiment," "in an embodiment," and similar phrases throughout this specification may, but do not necessarily, refer to the same embodiment.

Furthermore, the described features, operations, structures, or characteristics of the described embodiments may be combined in any suitable manner. Hence, the numerous details provided here, such as examples of electrode configurations, housing configurations, substrate configurations, channel configurations, catalyst configurations, and so forth, provide an understanding of several embodiments of the invention. For example, the substrates 612, 630 of FIGS. 10a-11b may be formed as an electronic chip having one or more materials from the group comprising silica, alumina, or other known chip materials. However, some embodiments may be practiced without one or more of the specific details, or with other features operations, components, materials, and so forth. In other instances, well-known structures, materials, or operations are not shown or described in at least some of the figures for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure provided herein. In other words, various modifications and improvements of the embodiments specifically disclosed in the description above are within the scope of the appended claims. The scope of the invention is therefore defined by the following claims.

What is claimed is:

1. An electrochemical probe for treatment of a tissue, the electrochemical probe comprising:
   a needle comprising a tip, the needle to penetrate the tissue within a body;
   a material treatment module coupled to the needle, the material treatment module located in the tip of the needle, the material treatment module comprising first and second electrodes to electrolyze an electrolyte between the first and second electrodes;
   a power source coupled to the first and second electrodes, the power source to supply a low frequency electrical potential to the first and second electrodes;
   an electrical conductor between the power source and one of the first and second electrodes; and
   an insulator material within the needle, the insulator material to insulate the electrical conductor from the needle.

2. The electrochemical probe of claim 1, further comprising an absorbent membrane disposed between the first and second electrodes, wherein the absorbent membrane is configured to at least partially contain the electrolyte.

3. The electrochemical probe of claim 2, wherein the absorbent membrane comprises a wick and the electrolyte comprises fluid.

4. The electrochemical probe of claim 3, wherein the fluid comprises water from the tissue.

5. The electrochemical probe of claim 1, wherein the material treatment module comprises an electrochemical cell to cause one of electro-oxidation and electro-reduction of a material of the tissue.

6. The electrochemical probe of claim 1, wherein an operating frequency of the low frequency electrical potential comprises a frequency less than about 200 kHz.

7. The electrochemical probe of claim 1, wherein the first electrode comprises at least a part of the needle.

8. The electrochemical probe of claim 1, further comprising a channel within the insulator material.

9. The electrochemical probe of claim 1, further comprising at least one channel within the needle to permit passage of electrolysis products through the needle and out of the electrochemical probe.

10. The electrochemical probe of claim 1, further comprising a plurality of apertures in the needle to allow a fluid to communicate with the tissue and the needle.

11. The electrochemical probe of claim 1, further comprising a substrate supported in the tip of the needle, wherein the first and second electrodes are located on the substrate.

12. The electrochemical probe of claim 1, wherein the electrolyte comprises a material chosen from at least one of air, oxygen, water, nitrogen, carbon dioxide, chlorine, bromine, and combinations thereof.

13. The electrochemical probe of claim 1, wherein the electrolyte comprises a salt solution chosen from NaI, NaF, NaCl, NaBr, and combinations thereof.

14. The electrochemical probe of claim 1, wherein the electrolyte comprises a salt having at least one cation chosen from $H^+$, $Li^+$, $Na^+$, $K^+$, $NH_4^+$, $Ca^+$, $Me^{++}$, $Sr^{++}$, $Ba^{++}$, and combinations thereof.

15. The method electrochemical probe of claim 1, wherein the electrolyte comprises a salt having at least one anion chosen from $F^-$, $Cl^-$, $Br^-$, $I^-$, $SO_4^{2-}$, $NO_3^{2-}$, $CO_3^{2-}$, $O^{2-}$, $S^{2-}$, $CH_3COO^-$ and combinations thereof.

16. The electrochemical probe of claim 1, wherein the electrolyte is in the form of a gas, liquid, gel, solid or combinations thereof.

17. An electrochemical probe for treatment of tissue, the probe comprising:
 a needle for penetrating a body to a target tissue, wherein the needle comprises a first electrode and has a tip;
 a second electrode at or near the tip of the needle;
 a wick disposed within the needle to hold an electrolyte during an electrolysis process; and
 a power source applying a low frequency electrical potential across the first and second electrodes.

18. An electrochemical probe for treatment of a tissue, the electrochemical probe comprising:
 a needle comprising a tip, the needle to penetrate the tissue within a body;
 a material treatment module coupled to the needle, the material treatment module located in the tip of the needle, the material treatment module comprising first and second electrodes to electrolyze an electrolyte between the first and second electrodes;
 an absorbent membrane disposed between the first and second electrodes, wherein the absorbent membrane is configured to at least partially contain the electrolyte; and
 a power source coupled to the first and second electrodes, the power source to supply a low frequency electrical potential to the first and second electrodes.

19. The electrochemical probe of claim 18, wherein the absorbent membrane comprises a wick and the electrolyte comprises fluid.

20. The electrochemical probe of claim 19, wherein the fluid comprises water from the tissue.

21. The electrochemical probe of claim 19, wherein the fluid comprises water from a source external to the tissue.

22. The electrochemical probe of claim 19, wherein the fluid comprises an organic solvent.

23. An electrochemical probe for treatment of a tissue, the electrochemical probe comprising:
 a needle comprising a tip, the needle to penetrate the tissue within a body;
 a material treatment module coupled to the needle, the material treatment module located in the tip of the needle, the material treatment module comprising first and second electrodes to electrolyze an electrolyte between the first and second electrodes, wherein the material treatment module further comprises an electrochemical cell to cause one of electro-oxidation and electro-reduction of a material of the tissue; and
 a power source coupled to the first and second electrodes, the power source to supply a low frequency electrical potential to the first and second electrodes.

24. An electrochemical probe for treatment of a tissue, the electrochemical probe comprising:
 a needle comprising a tip, the needle to penetrate the tissue within a body, wherein the needle further comprises a plurality of apertures in the needle to allow a fluid to communicate with the tissue and the needle;
 a material treatment module coupled to the needle, the material treatment module located in the tip of the needle, the material treatment module comprising first and second electrodes to electrolyze an electrolyte between the first and second electrodes; and
 a power source coupled to the first and second electrodes, the power source to supply a low frequency electrical potential to the first and second electrodes.

25. An electrochemical probe for treatment of a tissue, the electrochemical probe comprising:
 a needle comprising a tip, the needle to penetrate the tissue within a body;
 a material treatment module coupled to the needle, the material treatment module located in the tip of the needle, the material treatment module comprising first and second electrodes to electrolyze an electrolyte between the first and second electrodes, the material treatment module further comprising a substrate supported in the tip of the needle, wherein the first and second electrodes are located on the substrate; and
 a power source coupled to the first and second electrodes, the power source to supply a low frequency electrical potential to the first and second electrodes.

* * * * *